US011941050B2

(12) United States Patent
Barral et al.

(10) Patent No.: US 11,941,050 B2
(45) Date of Patent: *Mar. 26, 2024

(54) SYSTEMS AND METHODS FOR SEGMENTING SURGICAL VIDEOS

(71) Applicant: Verily Life Sciences LLC, South San Francisco, CA (US)

(72) Inventors: Joëlle K. Barral, Mountain View, CA (US); Martin Habbecke, Palo Alto, CA (US); Michal Levin, Mountain View, CA (US); Antons Krumins, Mountain View, CA (US); Thomas Teisseyre, Pacifica, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/176,795

(22) Filed: Feb. 16, 2021

(65) Prior Publication Data
US 2021/0200804 A1 Jul. 1, 2021

Related U.S. Application Data

(63) Continuation of application No. 16/162,898, filed on Oct. 17, 2018, now Pat. No. 10,956,492.

(Continued)

(51) Int. Cl.
*G06F 16/738* (2019.01)
*A61B 34/20* (2016.01)
(Continued)

(52) U.S. Cl.
CPC ............ *G06F 16/739* (2019.01); *A61B 34/20* (2016.02); *A61B 90/37* (2016.02); *G16H 30/40* (2018.01);
(Continued)

(58) Field of Classification Search
None
See application file for complete search history.

(56) References Cited

U.S. PATENT DOCUMENTS

| 5,801,685 A | 9/1998 | Miller et al. |
| 6,535,639 B1 | 3/2003 | Uchihachi et al. |
| (Continued) | | |

FOREIGN PATENT DOCUMENTS

| CN | 1520561 | 8/2004 |
| CN | 1666510 | 9/2005 |
| (Continued) | | |

OTHER PUBLICATIONS

Author: Krader et al.; Title: Endoscopy offers valuable adjunct in cataract surgery; Date: Jan. 1, 2014; Source: Ophthalmology Times https://www.ophthalmologytimes.com/view/endoscopy-offers-valuable-adjunct-cataractsurgery (Year: 2014).*

(Continued)

*Primary Examiner* — Jwalant Amin
(74) *Attorney, Agent, or Firm* — Kilpatrick Townsend & Stockton LLP

(57) ABSTRACT

Systems and methods for segmenting surgical videos are disclosed. One example method includes receiving, by a processor of a computing device, surgical video, the surgical video comprising at least a sequence of video frames of a surgical procedure; in response to receiving an identification of a video frame, generating, by the processor, a bookmark based on the video frame; associating, by the processor, the bookmark with the video frame; and storing, by the processor, the bookmark in a non-transitory computer-readable medium.

30 Claims, 19 Drawing Sheets

Related U.S. Application Data

(60) Provisional application No. 62/573,327, filed on Oct. 17, 2017.

(51) Int. Cl.
| | | |
|---|---|---|
| *A61B 90/00* | (2016.01) | |
| *G16H 30/40* | (2018.01) | |
| *A61B 34/00* | (2016.01) | |
| *A61B 34/10* | (2016.01) | |
| *G11B 27/34* | (2006.01) | |
| *H04N 21/472* | (2011.01) | |
| *H04N 21/845* | (2011.01) | |
| *H04N 21/858* | (2011.01) | |

(52) U.S. Cl.
CPC ......... *A61B 2034/107* (2016.02); *A61B 34/25* (2016.02); *G11B 27/34* (2013.01); *H04N 21/47217* (2013.01); *H04N 21/8456* (2013.01); *H04N 21/858* (2013.01)

(56) References Cited

U.S. PATENT DOCUMENTS

| | | |
|---|---|---|
| 7,231,135 B2 | 6/2007 | Esenyan et al. |
| 7,398,000 B2 | 7/2008 | Green |
| 8,638,056 B2 | 1/2014 | Goldberg et al. |
| 8,953,928 B2 | 2/2015 | Beacham et al. |
| 9,171,477 B2 | 10/2015 | Luo et al. |
| 9,396,669 B2 | 7/2016 | Karkanias et al. |
| 9,485,475 B2 | 11/2016 | Speier et al. |
| 10,592,750 B1 | 3/2020 | Yavagal et al. |
| 2002/0069218 A1 | 6/2002 | Sull et al. |
| 2002/0163532 A1 | 11/2002 | Thomas et al. |
| 2003/0086691 A1* | 5/2003 | Yu .................. G11B 27/34 386/243 |
| 2003/0234803 A1 | 12/2003 | Toyama et al. |
| 2007/0288426 A1 | 12/2007 | Schachter |
| 2008/0131853 A1 | 6/2008 | Kunitz |
| 2008/0316304 A1 | 12/2008 | Claus et al. |
| 2009/0210779 A1 | 8/2009 | Badoiu et al. |
| 2009/0327856 A1 | 12/2009 | Mouilleseaux et al. |
| 2010/0115596 A1 | 5/2010 | Horozov et al. |
| 2010/0199295 A1 | 8/2010 | Katpelly et al. |
| 2011/0044538 A1 | 2/2011 | Vanderhoff |
| 2011/0119392 A1 | 5/2011 | Shamilian et al. |
| 2012/0057847 A1 | 3/2012 | Casagrande |
| 2012/0155834 A1* | 6/2012 | Beacham ......... H04N 21/47217 386/E5.003 |
| 2012/0263430 A1 | 10/2012 | Spitzer-Williams |
| 2014/0286533 A1 | 9/2014 | Luo et al. |
| 2015/0086947 A1 | 3/2015 | Schweid et al. |
| 2015/0297299 A1 | 10/2015 | Yeung et al. |
| 2016/0014479 A1 | 1/2016 | Gower et al. |
| 2016/0314717 A1 | 10/2016 | Grubbs |
| 2016/0322081 A1 | 11/2016 | Schileru |
| 2017/0053543 A1 | 2/2017 | Agrawal et al. |
| 2017/0330598 A1* | 11/2017 | Choi ................ G11B 27/32 |
| 2018/0047429 A1 | 2/2018 | Smith |
| 2018/0176661 A1 | 6/2018 | Varndell et al. |
| 2018/0247128 A1 | 8/2018 | Alvi et al. |
| 2018/0322949 A1 | 11/2018 | Mohr et al. |
| 2019/0090969 A1 | 3/2019 | Jarc et al. |
| 2019/0110856 A1 | 4/2019 | Barral et al. |
| 2019/0279765 A1 | 9/2019 | Giataganas et al. |
| 2019/0286652 A1 | 9/2019 | Habbecke et al. |
| 2020/0194111 A1 | 6/2020 | Venkataraman et al. |
| 2020/0268457 A1 | 8/2020 | Wolf et al. |

FOREIGN PATENT DOCUMENTS

| | | |
|---|---|---|
| CN | 101127870 | 2/2008 |
| CN | 105518783 | 4/2016 |
| JP | 2002044586 | 2/2002 |
| KR | 101352999 | 2/2014 |
| WO | 2015114196 A1 | 8/2015 |
| WO | 2017083768 A1 | 5/2017 |

OTHER PUBLICATIONS

Chinese Application No. 201880067999.8, Office Action, dated Jun. 15, 2021, 11 pages.
Sun et al., "Engineering a Video Analysis-based E-book Turning System", Journal of Shaanxi University of Science and Technology, vol. 29, No. 4, Aug. 2011, pp. 24-28 (English abstract).
Application No. CN201880067999.8 , Notice of Decision to Grant, dated Dec. 29, 2021, 4 pages.
Application No. JP2020-518783 , Office Action, dated Jan. 14, 2022, 3 pages.
U.S. Appl. No. 16/162,898, "Final Office Action", dated Jul. 10, 2020, 45 pages.
U.S. Appl. No. 16/162,898, "Non-Final Office Action", dated Jan. 9, 2020, 32 pages.
U.S. Appl. No. 16/162,898, "Notice of Allowance", dated Oct. 30, 2020, 9 pages.
U.S. Appl. No. 16/162,898, "Supplemental Notice of Allowability", dated Feb. 9, 2021, 4 pages.
Chen, "How to Bookmark and Share Specific Portions of an Online Video", Available online at: https://www.guidingtech.com/5116/share-specific-parts-of-youtube-video-blipsnips/, Sep. 2, 2010, pp. 1-3.
Guggenberger, et al., "Event Understanding in Endoscopic Surgery Videos", Proceedings of the 1st ACM International Workshop on Human Centered Event Understanding from Multimedia, Nov. 2014, pp. 17-22.
Patkar, "5 Better Alternatives to Pocket that Bookmark Anything for Later", Available Online at: https://www.makeuseof.com/tag/better-alternatives-pocket-bookmark-anything-later/, Apr. 15, 2017, pp. 1-9.
PCT/US2018/056260, "International Preliminary Report on Patentability", dated Apr. 30, 2020, 9 pages.
PCT/US2018/056260, "International Search Report and Written Opinion", dated Jan. 29, 2019, 13 pages.
PCT/US2020/022540, "International Search Report and Written Opinion", dated Jul. 2, 2020, 13 pages.
PCT/US2020/022540, "Invitation to Pay Additional Fees and, Where Applicable, Protest Fee", dated May 7, 2020, 2 pages.
U.S. Appl. No. 16/807,629 , Non-Final Office Action, dated Sep. 9, 2021, 17 pages.
Du et al., "Patch-Based Adaptive Weighting with Segmentation and Scale (PAWSS) for Visual Tracking in Surgical Video", Medical Image Analysis, vol. 57, Jul. 4, 2019, pp. 120-135.
Jin et al., "Tool Detection and Operative Skill Assessment in Surgical Videos Using Region-Based Convolutional Neural Networks", IEEE Winter Conference on Applications of Computer Vision, May 7, 2018, 9 pages.
Münzer et al., "Relevance Segmentation of Laparoscopic Videos", IEEE International Symposium on Multimedia, Feb. 24, 2014, 8 pages.
Canadian Application No. 3,079,559, "Office Action", dated Nov. 30, 2022, 4 pages.
U.S. Appl. No. 17/720,414 , "Non-Final Office Action", dated Apr. 17, 2023, 15 pages.
Canadian Application No. 3,079,559 , "Office Action", dated May 12, 2023, 4 pages.
U.S. Appl. No. 17/720,414 , "Notice of Allowance", dated Jul. 26, 2023, 9 pages.
European Application No. 18797398.7 , "Office Action", dated Aug. 17, 2023, 12 pages.
Twinanda et al., "Classification Approach for Automatic Laparoscopic Video Database Organization", International Journal of Computer Assisted Radiology and Surgery, vol. 10, No. 9, Apr. 7, 2015, pp. 1449-1460.

(56) References Cited

OTHER PUBLICATIONS

Canadian Application No. 3,079,559 , "Office Action", dated Oct. 27, 2023, 5 pages.

* cited by examiner

Metadata
600

```
                <video_annotations>

610 →           <video>GastricBypass_DrSamBrown_141120171630.mp4</video>

612 →           <type>Gastric_Bypass</type>
                <subtype>Hi_BMI</subtype>

<title>Gastric Bypass – High BMI</title>
620 →           <surgeon>Dr. Sam Brown</surgeon>
                <date>11/14/2017</date>
                <time>16:30<time>

<bookmark>
622a →              <step>Bypass_Pouch_Create</step>     ← 624
                    <name>Creation of Pouch</name>       ← 625
                    <begin>3:02.0</begin>                ← 626
                    <end>22:12.12</end>                  ← 627
                </bookmark>
                <bookmark>
622b →              <step>Bypass_GastroJJ_Anastomosis</step>
                    <name>Gastrojejunal Anastomosis</name>
                    <begin>22:12.13</begin>
                    <end>38:04.6</end>
                </bookmark>
                <bookmark>
622c →              <step>Bypass_Measure_Al_Limb</step>
                    <name>Measurement of Alimentary Limb</name>
                    <begin>38:04.7</begin>
                    <end>52:16.21</end>
                </bookmark>
                <bookmark>
622d →              <step>Bypass_Create_JJ_Anastomosis</step>
                    <name>Create Jejunal Anastomosis</name>
                    <begin>52:16.22</begin>
                    <end>1:02:56.13</end>
                </bookmark>
                <bookmark>
622e →              <begin>1:02:56.14</begin>
                </bookmark>

</video_annotations>
```

*FIG. 6*

SYSTEMS AND METHODS FOR SEGMENTING SURGICAL VIDEOS

CROSS-REFERENCE TO RELATED APPLICATIONS

This application is a continuation of U.S. patent application Ser. No. 15/331,097, filed Oct. 21, 2016, titled "Systems and Methods for Monitoring Medication Adherence and Compliance," now U.S. Pat. No. 10,456,326, the entirety of which is hereby incorporated by reference.

FIELD

This disclosure relates generally to systems for performing surgery, and in particular but not exclusively, relates to systems and methods for segmenting surgical videos.

BACKGROUND

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of open surgery, robotically controlled instruments may replace traditional tools to perform surgical motions. Feedback controlled motions may allow for smoother surgical steps than those performed by humans. For example, using a surgical robot for a step such as rib spreading, may result in less damage to the patient's tissue than if the step were performed by a surgeon's hand. Additionally, surgical robots can reduce the amount of time in the operating room by requiring fewer steps to complete a procedure.

However, robotic surgery may still suffer from limitations associated with conventional surgery. For example, surgeons may still need to review surgical videos in order to become comfortable with a procedure. And it may take days or weeks before the surgeon views enough footage in order to become proficient with a particular type of surgery.

SUMMARY

Various examples are described for systems and methods for segmenting surgical videos. One example method for segmenting surgical videos includes receiving, by a processor of a computing device, surgical video, the surgical video comprising at least a sequence of video frames of a surgical procedure; in response to receiving an identification of a video frame, generating, by the processor, a bookmark based on the video frame; associating, by the processor, the bookmark with the video frame; and storing, by the processor, the bookmark in a non-transitory computer-readable medium.

Another example method for segmenting surgical videos includes receiving a surgical video and at least one bookmark, each bookmark identifying a different video frame within the surgical video; receiving an identification of a first bookmark; receiving an indication to extract a portion of the surgical video; extracting the portion of the surgical video, the portion of the surgical video beginning at the first bookmark; and storing the portion of the surgical video in a non-transitory computer-readable medium.

A further example method for segmenting surgical videos includes receiving a search command comprising a search parameter, the search parameter comprising one of (i) an step of a surgical procedure, (ii) a sub-step of the surgical procedure, or (iii) an event of the surgical procedure; accessing bookmark information for a plurality of surgical videos; identifying a plurality of bookmarks using the search parameter, each bookmark of the plurality of bookmarks associated with one of the surgical videos; and providing a subset of the plurality of bookmarks in response to the search command.

One example system for segmenting surgical videos includes a non-transitory computer-readable medium; and a processor in communication with the non-transitory computer-readable medium, the processor configured to execute processor-executable instructions stored in the non-transitory computer-readable medium to receive surgical video, the surgical video comprising at least sequence of video frames of a surgical procedure; in response to receiving an identification of a video frame, generate a bookmark based on the video frame; associate the bookmark with the video frame; and store the bookmark.

Another example system for segmenting surgical videos includes a non-transitory computer-readable medium; a processor in communication with the non-transitory computer-readable medium and configured to execute processor-executable instructions stored in the non-transitory computer-readable medium to receive a surgical video and a plurality of bookmarks identifying different video frames within the surgical video; receive an identification of a first bookmark of the plurality of bookmarks; receive a command to extract a portion of the surgical video; extract the portion of the surgical video, the portion of the surgical video beginning at the video frame; and store the portion of the surgical video in a non-transitory computer-readable medium.

A further example system for segmenting surgical videos includes a non-transitory computer-readable medium; and a processor in communication with the non-transitory computer-readable medium and configured to execute processor-executable instructions to receive a search command comprising a search parameter, the search parameter comprising one of (i) an step of a surgical procedure, (ii) a sub-step of the surgical procedure, or (iii) an event of the surgical procedure; access bookmark information for a plurality of surgical videos; identify a plurality of bookmarks using the search parameter, each bookmark of the plurality of bookmarks associated with one of the surgical videos; and provide a subset of the plurality of bookmarks in response to the search command.

One example non-transitory computer-readable medium for segmenting surgical videos includes processor-executable instructions configured to cause a processor to receive surgical video, the surgical video comprising at least sequence of video frames of a surgical procedure; in response to receiving an identification of a video frame, generate a bookmark based on the video frame; associate the bookmark with the video frame; and store the bookmark.

Another example non-transitory computer-readable medium for segmenting surgical videos includes processor-executable instructions configured to cause a processor to receive a surgical video and a plurality of bookmarks identifying different video frames within the surgical video; receive an identification of a first bookmark of the plurality of bookmarks; receive a command to extract a portion of the surgical video; extract the portion of the surgical video, the portion of the surgical video beginning at the video frame; and store the portion of the surgical video in a non-transitory computer-readable medium.

A further example non-transitory computer-readable medium for segmenting surgical videos includes receive a search command comprising a search parameter, the search parameter comprising one of (i) an step of a surgical procedure, (ii) a sub-step of the surgical procedure, or (iii) an event of the surgical procedure; access bookmark information for a plurality of surgical videos; identify a plurality of bookmarks using the search parameter, each bookmark of the plurality of bookmarks associated with one of the surgical videos; and provide a subset of the plurality of bookmarks in response to the search command.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 6 shows example metadata for segmenting surgical videos;

DETAILED DESCRIPTION

Figure 1:
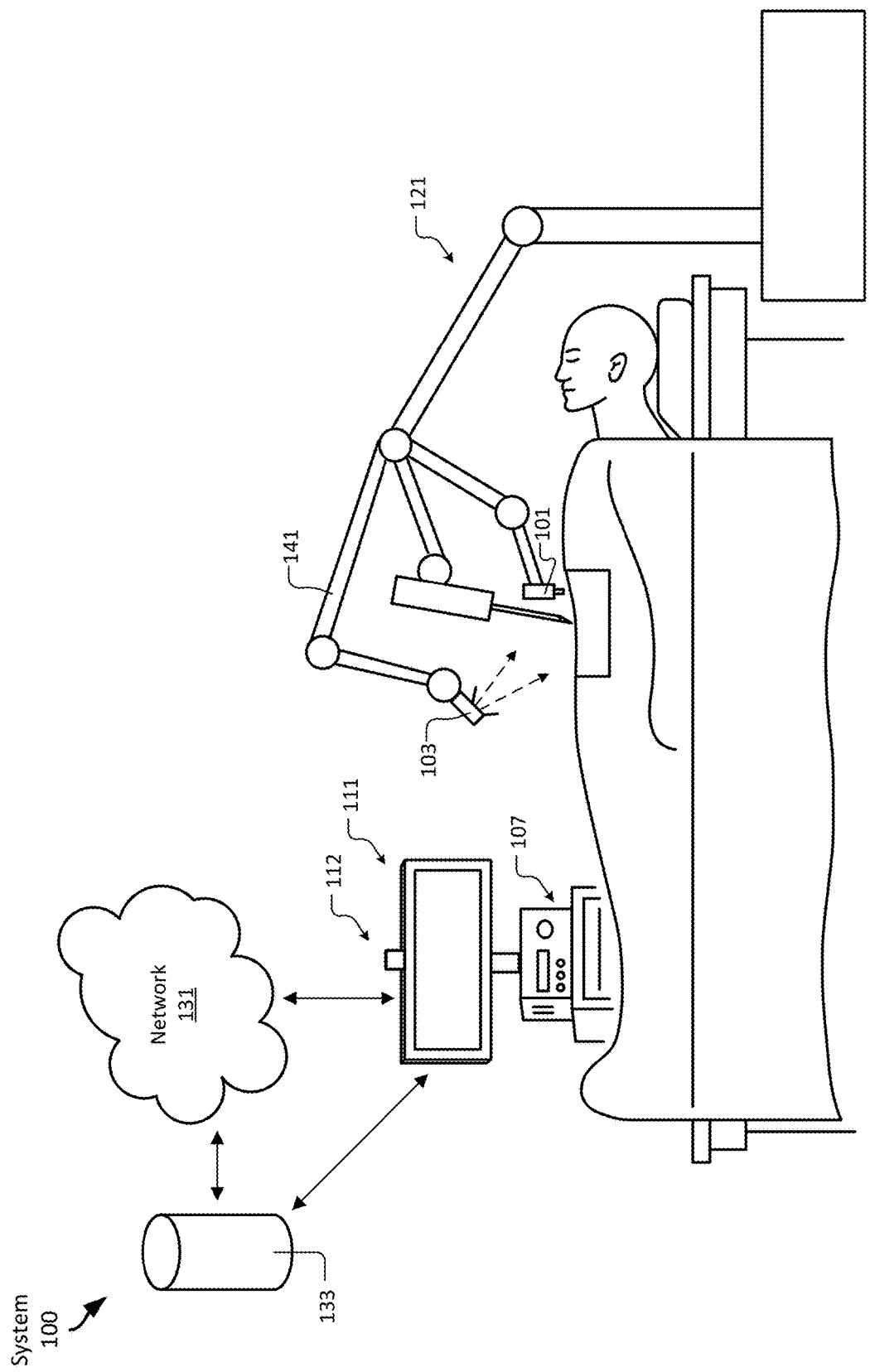
FIGS. 1-2 and 3A-3B show example systems for segmenting surgical videos.

Examples are described herein in the context of systems and methods for segmenting surgical videos. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Most surgical procedures take hours to complete and the corresponding videos are so long that they are unlikely to be viewed in their entirety ever again. Further, while reviewing such videos may be a valuable way to learn techniques, review unexpected events, or assess mistakes made during the procedure, searching a single video for relevant information is tedious and requires manually fast-forwarding or rewinding, commonly referred to as "scrubbing." Once video of interest is identified, it may be manually extracted from the full video using conventional video editing tools, such as by manually selecting the start and end points and using the tool to extract the section of video. However, if multiple segments of video are extracted from the same original video as being of interest to the particular procedure, the several different files must be separately managed and maintained, such as in a folder on a file system, and if a surgeon wants to later view these different parts of the original video, she must manually select each individual video and watch them independently of each other. Similarly, sharing video with others requires either sending extracted video by email or bulk file transfer or providing a link to an online copy of the video.

To reduce the burden on surgeons who might otherwise be required manually process their own video, or other surgical videos they access, an illustrative system enables various techniques to allow the surgeon, or a machine-learning ("ML") technique, to quickly bookmark points within a surgical video, share those bookmarks, excerpt video(s) from the full video using the bookmarks, to identify the type of surgical procedure and the steps, sub-steps, or events of interest within the surgical procedure. Such techniques may allow surgeons to more efficiently review surgical videos, improve their surgical techniques, assess errors and corrective actions or training needs, or search a corpus of videos for specific portions of surgical videos, such as for specific steps of a particular type surgical procedure or events that occurred during one or more surgical procedures.

This illustrative system in this example includes a video processing server that has access to surgical videos, such as from one or more robotic surgical systems (each an "RSS"). The RSSes record video from one or more endoscopic cameras during the course of various surgical procedures, stores the videos locally and later transfers them to a remote storage device, or it may stream them to remote storage during the respective surgical procedure.

The video processing server includes several trained ML techniques that are capable of recognizing different types of surgical procedures and, when presented with a new surgical video, can classify the video for further processing. The ML techniques are also capable of identifying surgical steps that may be employed in such surgical procedures. In this example, after the type of surgical procedure had been identified, a second ML technique that has been trained for that surgical procedure type is then used to identify the different steps taken within the video. This second trained ML technique outputs timestamps representing when the different steps of the procedure started and ended. After receiving this information from the second trained ML technique, the video processing server generates bookmarks and inserts them as metadata within the video file. Each bookmark includes the name of the respective step of the surgical procedure and a timestamp indicating the beginning of the respective step.

Once a surgical video has been bookmarked, it may notify the surgeon (or surgeons) involved in the procedure that the video has been processed and is available for review. At this time, the surgeon may access the processed video via a web portal interface. The web portal provides the surgeon with her videos from past surgical procedures and also gives access to other surgical videos available within the medical center, hospital network, etc.

When the surgeon first accesses the newly bookmarked video, she is presented with an interface that devotes part of the screen to the video itself. In addition, the interface provides a timeline for the video that can be used to scrub through the video. The timeline also includes markers indicating each of the bookmarks applied by the video processing server. The surgeon may select a bookmark to jump to the corresponding portion of the video and watch the bookmarked video segment. The markers are unlabeled by default, but if the surgeon hovers a cursor over a marker, the associated surgical step will be displayed. The surgeon also has the option of displaying a list of the bookmarks in the video and corresponding information, such as the name of the surgical step and the timestamp at which it begins within the video.

In addition to navigating directly to a video segment of interest, the bookmarks may also be used to further manipulate the video. For example, if the surgeon wishes to share a segment of the video with a colleague, she can select a bookmarks, or multiple bookmarks, and select a "share" option to generate a message to the colleague including a reference to the video and the bookmark. The message would then allow the recipient to jump to the bookmarked location within the video.

Alternatively, the surgeon can select one or more segments of video by selecting the corresponding bookmarks and selecting an option to extract the segment(s) of video. The segments may then be separately (or jointly) shared with the colleague, such as by attaching them to an email or a direct message via social media or multimedia messaging service, or simply maintained on the server for the surgeon (or others) to review, such as by storing the segments and associating each with the source video. Further, the video segments may also be indexed for searching based on their source video, bookmark information associated with each (e.g., steps, sub-steps, events, etc.), and the surgeon or surgeons that performed the surgical procedure.

This illustrative example provides numerous benefits to the creation and use of surgical video. For example, this example system can help surgeons looking to obtain training on a particular type of surgical procedure, as well as post-surgery analysis of any problems or issues that arose, or to assess the performance of a surgeon, such as a medical student, resident, etc. In addition, by employing ML techniques to perform preprocessing of surgical videos, videos can be made useful without burdening surgeons to manually review hours of surgical videos to find events of interest or different steps of a surgical procedure, or extract and share that video with colleagues or students.

This illustrative example is given to introduce the reader to the general subject matter discussed herein and the disclosure is not limited to this example. The following sections describe various additional non-limiting examples and examples of systems and methods for segmenting surgical videos.

Referring now to FIG. 1, FIG. 1 shows an example system 100 for segmenting surgical videos. System 100 includes surgical robot 121 (including one or more arms 141), camera 101, light source 103, computing device 107, display 111, network 131 (representing one or more networks), microphone 112, and data store 133, which includes one or more non-transitory computer-readable media to store video, audio, and other data gathered during surgical procedures. As shown, surgical robot 121 may be used to hold surgical instruments (e.g., each arm 141 may hold an instrument at the distal end of the arm) and perform surgery, diagnose disease, take biopsies, or conduct any other procedure a doctor or surgeon could perform. Surgical instruments may include scalpels, forceps, energy tools (e.g., to cauterize tissue), cameras (e.g., camera 101), or the like. While this example surgical robot 121 only has three arms 141, it should be appreciated that surgical robot 121 is merely a representative illustration, and that a surgical robot 121 can take any number of shapes, include any number of arms or tools, etc., depending on the type of surgery to be performed, etc. Surgical robot 121 may be coupled to computing device 107, network 131, and/or data store 133 either by wires or wirelessly. Furthermore, surgical robot 121 may be coupled (wirelessly or by a wired connection) to a user input device to receive instructions from a surgeon or doctor. Suitable user input devices include touch-sensitive screens, joysticks, foot pedals, hand-held devices or controllers, etc., and may include any input device used to control one or more surgical tools of the surgical robot 121 or to interact with the computing device 107, e.g., via a touch-sensitive display.

Computing device 107, and the user of computing device 107, may be located very close to the surgical robot 121 and patient (e.g., in the same room) or may be located many miles apart, such as in the case of a telesurgical operation. Thus surgical robot 121 may be used to perform surgery where a specialist is many miles away from the patient, and instructions from the surgeon are sent over the internet or another network (e.g., a secure network), such as network 131. Alternatively, the surgeon may be local and may manually control the surgical robot 121 using one or more input devices, such as pedals, joysticks, etc.

In the depicted embodiment, data store 133 may be included in one or more servers connected to the internet, generally referred to as "cloud" servers or "cloud" storage. Alternatively data store 133 may be local storage such as a hard drive, solid-state memory, or the like, located in the operating room or at the surgical center. Data store 133 may be coupled to network 131 which may include the internet or a local area network. It is appreciated that data store 133 and network 131 may be considered part of computing device 107. Thus the computing device 107 may be a distributed system in some examples. Network 131 and data store 133 may provide logic to computing device 107 that when executed by computing device 107 causes system 100 to perform a variety of operations. Alternatively or additionally, computing device 107 may include the processor and memory of a general purpose computer.

In the depicted embodiment, computing device 107, with one or more displays 111 and a microphone 112, is coupled to surgical robot 121. As shown, camera 101 is coupled to capture surgical video. A surgical video includes video captured during a surgical procedure, such as one performed with the surgical robot 121. The computing device 107 receives video signals from the camera, including any associated metadata generated at or by the camera, and stores the video signals in a video file, either locally at the computing device 107 or streamed to a remote server, such as cloud storage. In addition, in this example, the computing device 107 provides video signals to the display(s) 111, which displays the video during performance of the surgical procedure, such as to enable the surgeon to view the actions taken by the surgical robot 121. In some examples, the display(s) 111 may include one or more touch-sensitive displays capable of receiving touch inputs and providing touch input signals to the computing device 107, which may be employed to select options on the touch-sensitive display or to perform gestures on the touch-sensitive display (including multi-touch gestures).

After receiving the surgical video, either in real-time or after the entire video has been captured, computing device 107 then identifies segments in the surgical video by analyzing at least one of the surgical video or the associated metadata, and computing device 107 annotates the surgical video with annotations to identify each of the segments. In this example, the computing device 107 employs a ML technique to recognize the surgical procedure and to identify segments, or steps, of the surgical procedure. Any suitable ML technique may be trained to recognize different surgical procedures, such as a convolutional neural network ("CNN"), a long short-term memory ("LSTM") technique, a dynamic time warping ("DTW") technique, a hidden Markov model ("HMM"), or combinations of one or more of such techniques—e.g., CNN-LSTM, CNN-HMM or MCNN (Multi-Scale Convolutional Neural Network). The surgical video may then be output to display 111 with the annotations. This may allow the viewer of the surgical video to quickly identify and view the relevant portions of the video. Moreover, it can also provide annotated video feeds that can be used to further train one or more ML techniques.

Figure 2:
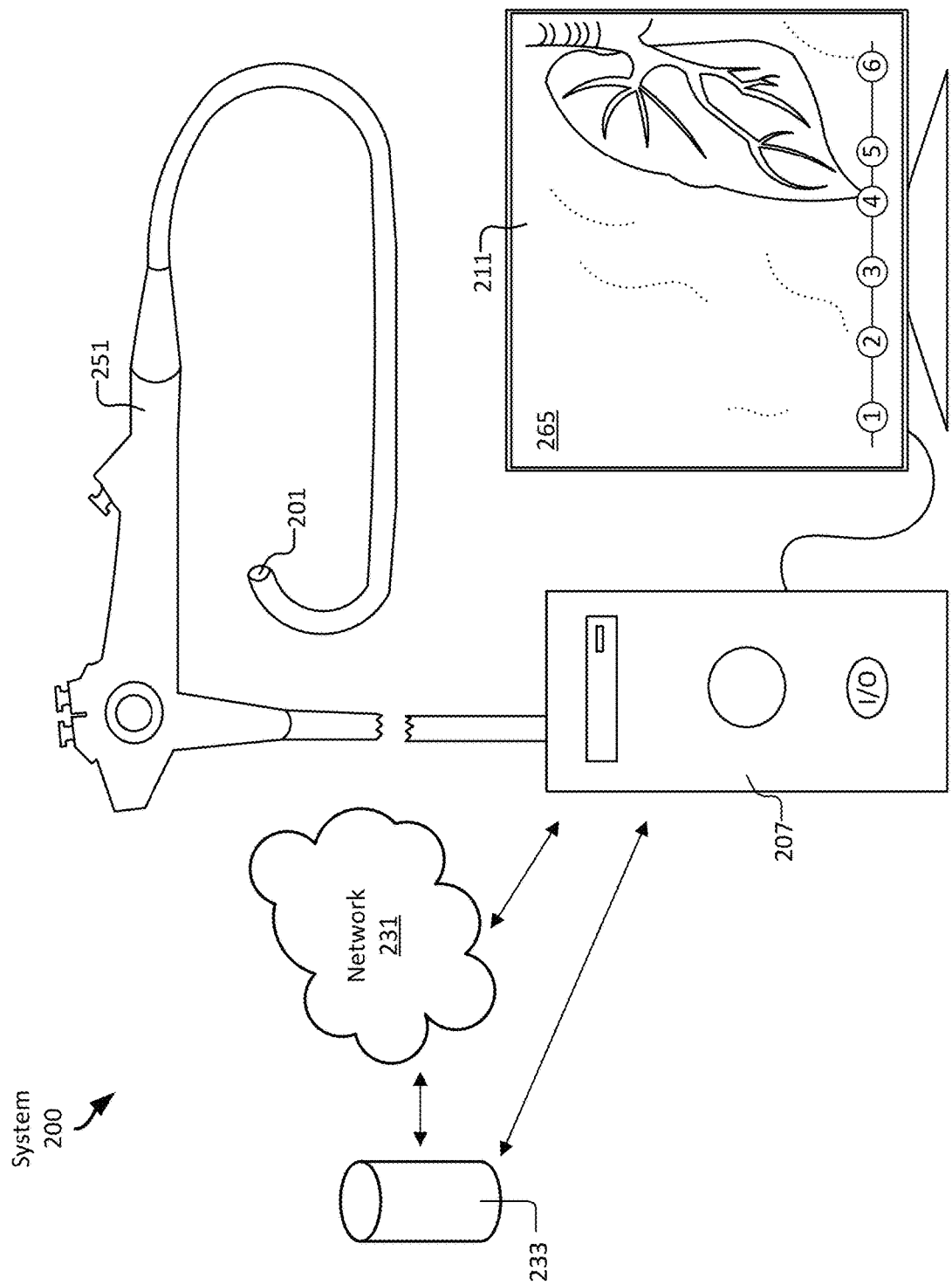

Referring now to FIG. 2, FIG. 2 shows an example system 200 for segmenting surgical video. In this example, the system 200 includes endoscope 251 (including camera 201), computing device 207, display 211, network 231, and storage 233. As depicted, camera 201 is disposed on the distal end (opposite the proximal end) of endoscope 251. Illumination sources may also be disposed to emit light from the distal end. Endoscope 251 is coupled to computing device 207 to output surgical video 265 to computing device 207. Like the example system 100 shown in FIG. 1, computing device 207 is coupled to a network 231 and storage 233. Computing device 207 is also coupled to a display 211 to output a temporally segmented, and annotated, video feed (shown with labels 1-6 on the play bar of video 265).

In this example, the endoscope 251 may capture video during an endoscopic surgery or the like (and thus may be considered a "surgical tool" for some examples), such as video 265 that includes video from a surgery on a patient's lung. The computing device 207 receives video signals from the camera 201 during the surgery, the video signals representing frames of video, and temporally segments and annotates the received video using one or more ML techniques. In this example, the segmenting and annotating is performed substantially in real-time as the video signals are received; however, in some examples, the video may be received and stored in a non-transitory computer-readable medium, either locally at the computing device 107 or remotely at storage 233, and after surgical procedure is completed, the video may be processed by one or more ML techniques. It should be appreciated that processing video in real-time can be computationally expensive and increases with the resolution of the captured video, thus, to alleviate some of the computational burden, the computing device 107 may not process every received frame of video, but may instead periodically sample video frames. For example, the computing device 207 may sample one frame per second and provide the frame to the ML technique for processing. In other examples, the computing device 207 may perform initial pre-processing at a higher rate, or on every frame, to determine if a frame has interesting features present and, if so, it may begin processing every frame or increase its sampling rate from the video feed, e.g., from 1 frame/second to 10 frames second, or even processing every received video frame.

For example, the computing device 207 may perform initial pre-processing, such as pre-processing one or more video frames, to determine whether the scene captured by the camera 201 has changed substantially since the last processed frame. If, for example, the surgeon has paused the surgical procedure to review patient records, confer with a colleague, or change a tool in a surgical robot, the computing device 207 may detect that two successively processed video frames are substantially the same, meaning a position or orientation of any surgical tools in-frame have not changed. Other inputs may be received indicating that likely no change in the video has occurred between successive frames. For example, if no inputs have been received from any surgical robot controls (e.g., no pedal has been pressed and no hand-held controller input has been detected) between the two frames, the surgeon has changed UI views from the endoscopic video to patient information, etc., the computing device 207 may determine that the scene has likely not changed and thus may not engage in further processing of the sampled video frame. Such pre-preprocessing may reduce the computational burden on the computing device 207, potentially enabling other functionality to be employed, such as segmenting or annotating previously captured video from the surgical procedure, etc. Alternatively, an ML technique may detect an interesting feature in a video frame, which may cause further processing to be performed on the video frame or to increase the rate at which video frames are sampled for processing by one or more ML techniques. Interesting features may include a video frame recognized by an ML technique as indicating a new step of a surgical procedure, a new sub-step of a surgical procedure, or a recognized event within the surgical procedure.

For example, if a bleeding event is detected, the computing device 207 may increase a sampling rate to process more frames likely to capture the bleeding event and any responses from the surgeon to the event. These frames may be processed to potentially capture other events or sub-steps occurring during the event. Alternatively, rather than processing such frames in real-time, the computing device may annotate one or more frames with metadata indicating the frames should be processed after the surgical procedure has been completed. Such annotations may include annotations on frames preceding the detected interesting feature since, the interesting feature may have begun prior to the frame in which it was detected. Thus, the computing device may generate annotated windows around potential events in real-time, but save the computationally expensive processing until after the surgical procedure has been completed.

In addition to adapting the video sampling or real-time processing to events occurring during surgery, such detected events may also be indicated in real-time on the display 211 as additional information for the surgeon. For example, a bleeding event may be visually indicated, such as with a textual display or with a graphical overlay on the detected bleeding, an arrow pointing to the bleeding, etc. In some examples, the detected step of the surgical procedure may be presented to the surgeon on the display for informational purposes. Further, in some examples, the surgeon may provide one or more inputs confirming that the detected step is in fact occurring, or may provide inputs indicating that the detected step is incorrect. Such information may be used to annotate the video or to further train one or more ML techniques, such as the ML technique resident in the computing device 207 or in a cloud server.

It should be appreciated that while the example system 200 discussed above includes a computing device 207 present locally within the operating room, other configurations employing remote servers, such as one or more cloud servers, may be suitable in some examples. For example, surgical video may be streamed from the camera 201 through the network 231 to a remote server for processing and storage, or to a remote telesurgery station where certain aspects of the functionality discussed above may be performed.

Figure 3:
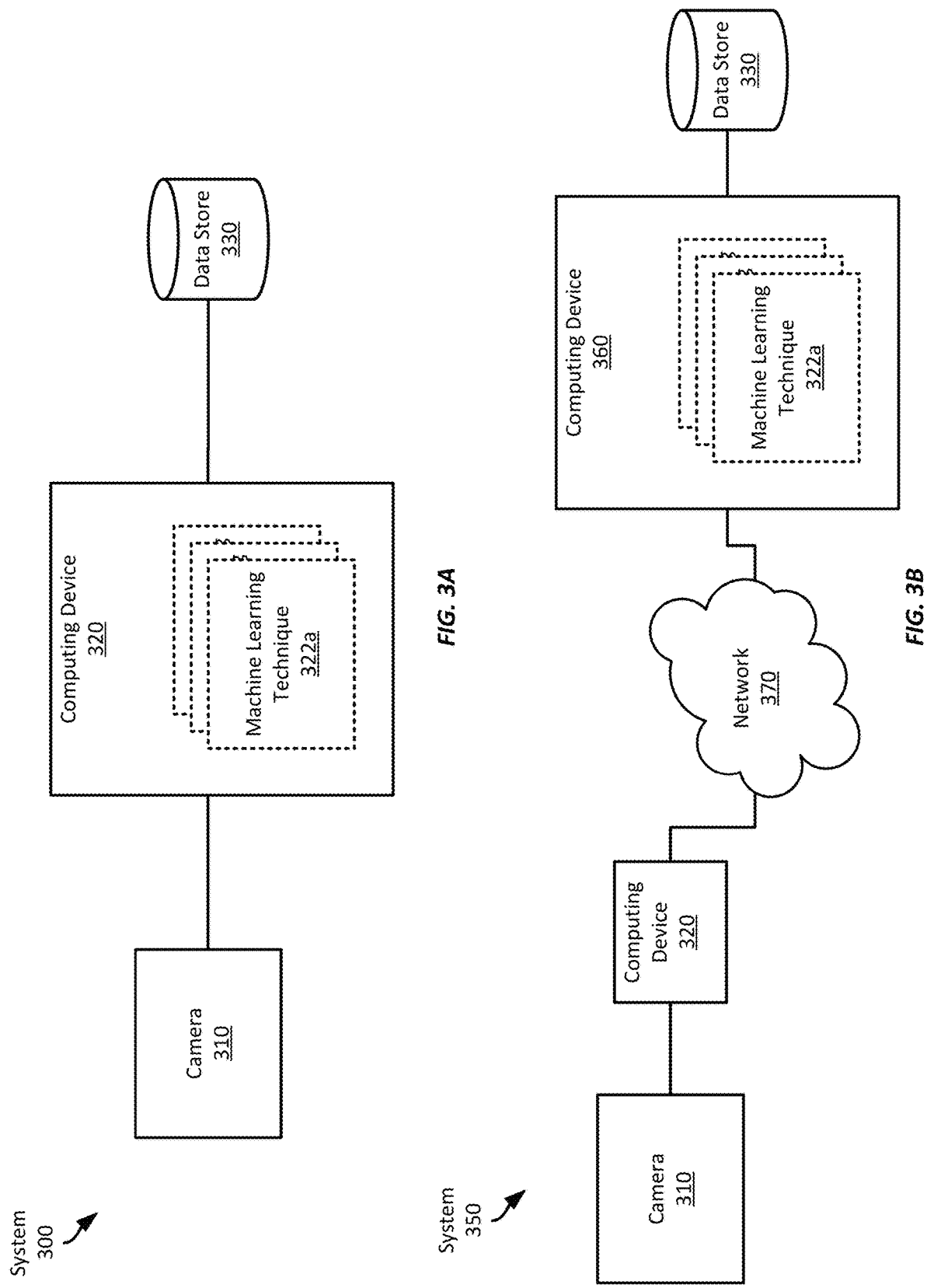

Referring now to FIGS. 3A-3B, FIG. 3A shows an example system 300 for segmenting surgical videos. The example system 300 includes a block diagram showing functional components. The system includes a camera 310, which is a part of a surgical robot (not shown). The camera 310 is connected to a computing device 320, which has one or more ML techniques 322*a-n* (where n is the number of ML techniques and may be any positive integer). The computing device receives video signals from the camera 310 and provides one or more sampled frames of video to one or more of the ML techniques 322*a-n*. For example, the computing device 320 may direct all video signals to one or more ML techniques 322*a-n*, which then individually sample discrete frames for processing, or the computing device 320 may sample the video signals and provide certain frames to the ML technique(s) 322*a-n* for processing. The computing device 320 also saves video information to the data store 330, which may include unprocessed or unannotated video or may include video that has been processed or annotated by one or more of the ML techniques 322*a-n*. While the data store 330 is shown as directly connected to the computing device 320 in this example, it should be understood that the data store 330 may be a cloud data store, or a data store connected to a remote server.

FIG. 3B shows an example system 350 that is a variant of the system 300 shown in FIG. 3A. In this example, the computing device 320 does not have the ML techniques 322*a-n*, but instead, receives video signals from the camera and transmits video information to a remote computing device 360 via one or more networks 370. The remote computing device 360 employs the ML techniques 322*a-n* to process or annotate the video information as will be discussed in more detail herein, which is then stored in the data store 330. Thus, in some examples, video captured by the camera 310 is processed remotely from the surgical procedure. Still further example configurations may be employed. For example, the camera 310 may transmit video signals via one or more networks 370 to a remote computing device 360 without the use of a local computing device 320.

Figure 4:
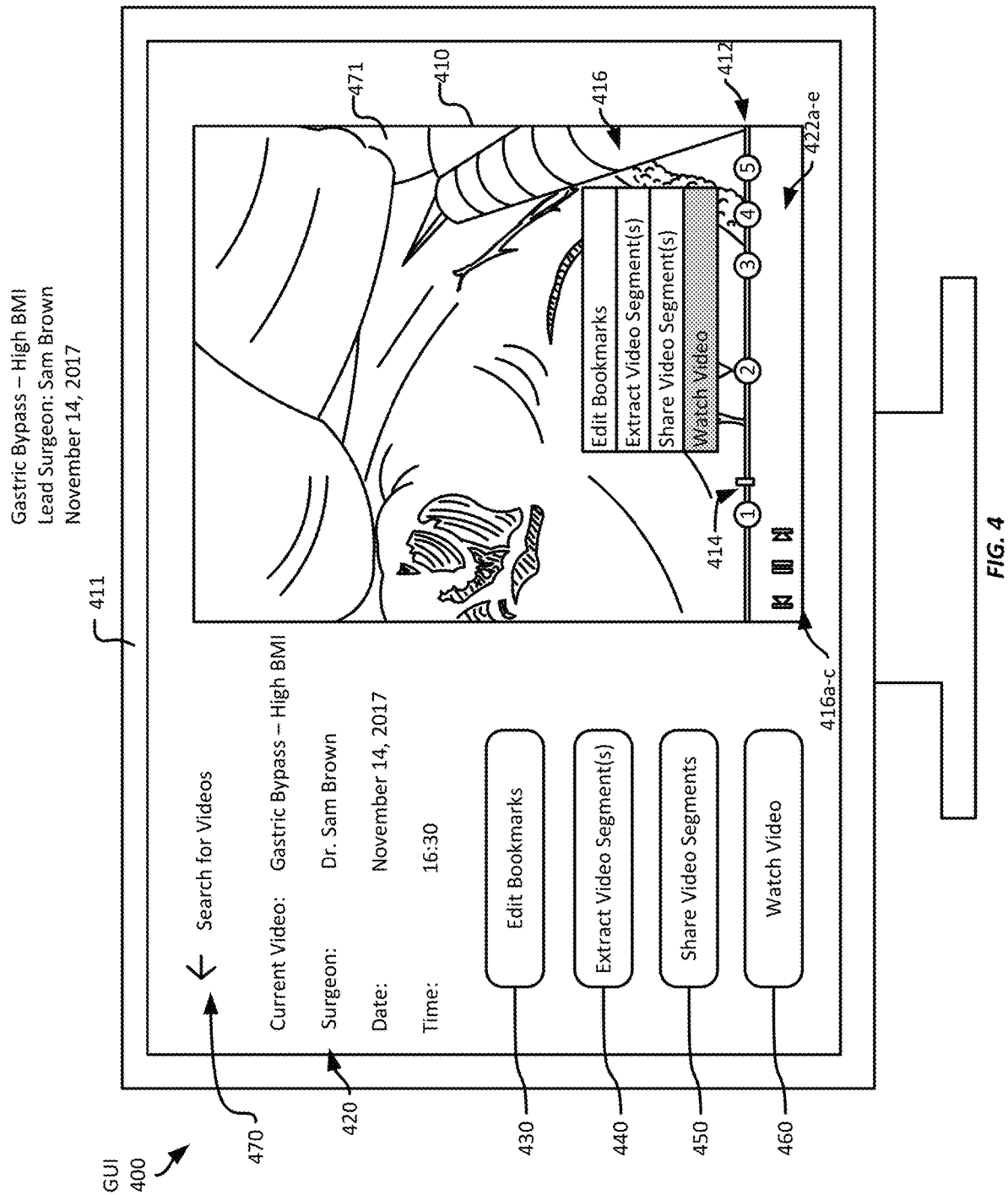
FIGS. 4 and 5 show example graphical user interfaces for segmenting surgical videos.

Referring now to FIG. 4, FIG. 4 shows an example graphical user interface ("GUI") 400 according to an example system for segmenting surgical videos. This example GUI 400 will be discussed with respect to the example system 100 shown in FIG. 1, but it should be appreciated that any suitable system according to this disclosure may be employed.

The GUI 400 shown in FIG. 4 is provided by an application executed by the computing device 107; however, in some examples, the GUI 400 may be provided as a web portal by a remote computing device, such as server 1140 in the system 1100 discussed below with respect to FIG. 11. In some examples, the GUI 400 may be provided by a native application executing on a computing device, such as the user devices 1110, 1120 or mobile device 1130 shown in FIG. 11. A web-portal-based GUI 400 may enable a user at a remote user terminal, e.g., user terminals 1110-1120 or mobile device 1130, to interact with the example GUI 400 (as well as other example GUIs discussed herein). This example GUI 400 is displayed on a display screen 411 and provides an interface for a user to interact with a surgical video 471. The GUI 400 includes a video window 410 that includes playback controls 416*a-c* to play/pause 416*b* the video 471, and segment skip forward/reverse buttons 416*a, c*. The video timeline 412 is shown with a cursor 414 showing the current frame of the video 471 in the timeline, which can be used to scrub through the video 471. In addition, five bookmarks 422*a-e* are positioned on the timeline 412 at locations corresponding to frames of the video 471. The bookmarks may be used to quickly jump to a particular frame of the video 471. Further, the skip forward/reverse buttons 416*a,c* may be used to jump between successive bookmarks, denoting different segments of the video 471.

In addition to allowing playback of the surgical video 471, the GUI 400 also provides bibliographic information 420 about the video, including the title, the lead surgeon, and the date and time of the surgery. Further, any other suitable bibliographic information may be included as well, including patient information, surgical robot information (e.g., tool configuration, manufacturer, model, etc.), medical center information, etc. In addition, the GUI 400 provides options to edit 430 bookmarks, extract 440 one or more video segments, share 450 video segments, or to watch 460 the video. Lastly, the GUI 400 provides the option to search 470 for other surgical videos. Such features are shown as buttons within the GUI, but may instead (or in addition) be presented within a context sensitive menu 416 within the video window 410. Such a context sensitive menu 416 may be accessed, e.g., by right clicking within the video or by right clicking on one or more bookmarks 422*a-e* on the timeline. Each of these features will be described in more detail in the following sections of this disclosure.

Figure 5:
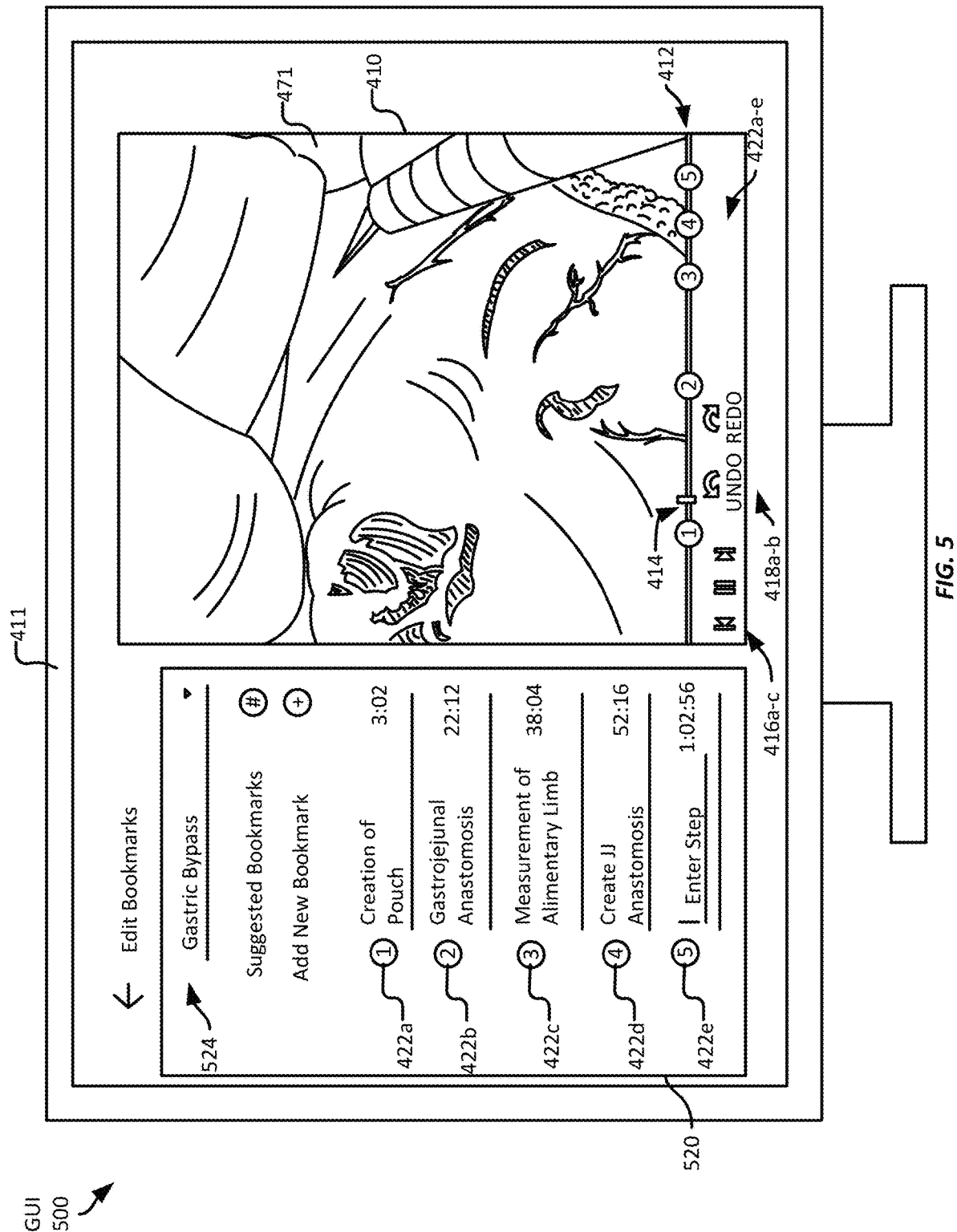

Referring now to FIG. 5, FIG. 5 shows an example GUI 500 according to an example system for segmenting surgical videos. This example GUI 500 will be discussed with respect to the example system 100 shown in FIG. 1, but it should be appreciated that any suitable system according to this disclosure may be employed.

The GUI 500 in this example provides functionality to segment surgical videos. The GUI include several user interface ("UI") components, including a video window 510 to show the surgical video 471. The video window 410 includes a video timeline 412 and a cursor 414 that may be used to manually scrub through the video 471. Video controls 416*a-c*, including pause, segment skip forward, and segment skip reverse, are also provided. In addition, "undo" and "redo" editing controls 518*a-b* are also provided to undo or redo bookmark changes. As can be seen, the video timeline 412 includes five bookmarks 422*a-e* that have been applied by a ML technique that processed the surgical video 471.

Each of the bookmarks 422*a-e* shown in the video window 410 are also replicated in the bookmark editor window 520 to the left of the video window 410. The bookmark editor window 520 allows a user to view detailed information about each bookmark and to edit one or more properties of each bookmark. In this example, the GUI 500 allows the user to supply names for each bookmark 422*a-e*, edit the position of each bookmark 422*a-e* within the video, see the exact timestamp associated with each bookmark, add or delete bookmarks, or specify the type of surgical procedure 524. In addition, the GUI 500 allows the user to return to a previous GUI screen to select different functionality.

Figure 8:
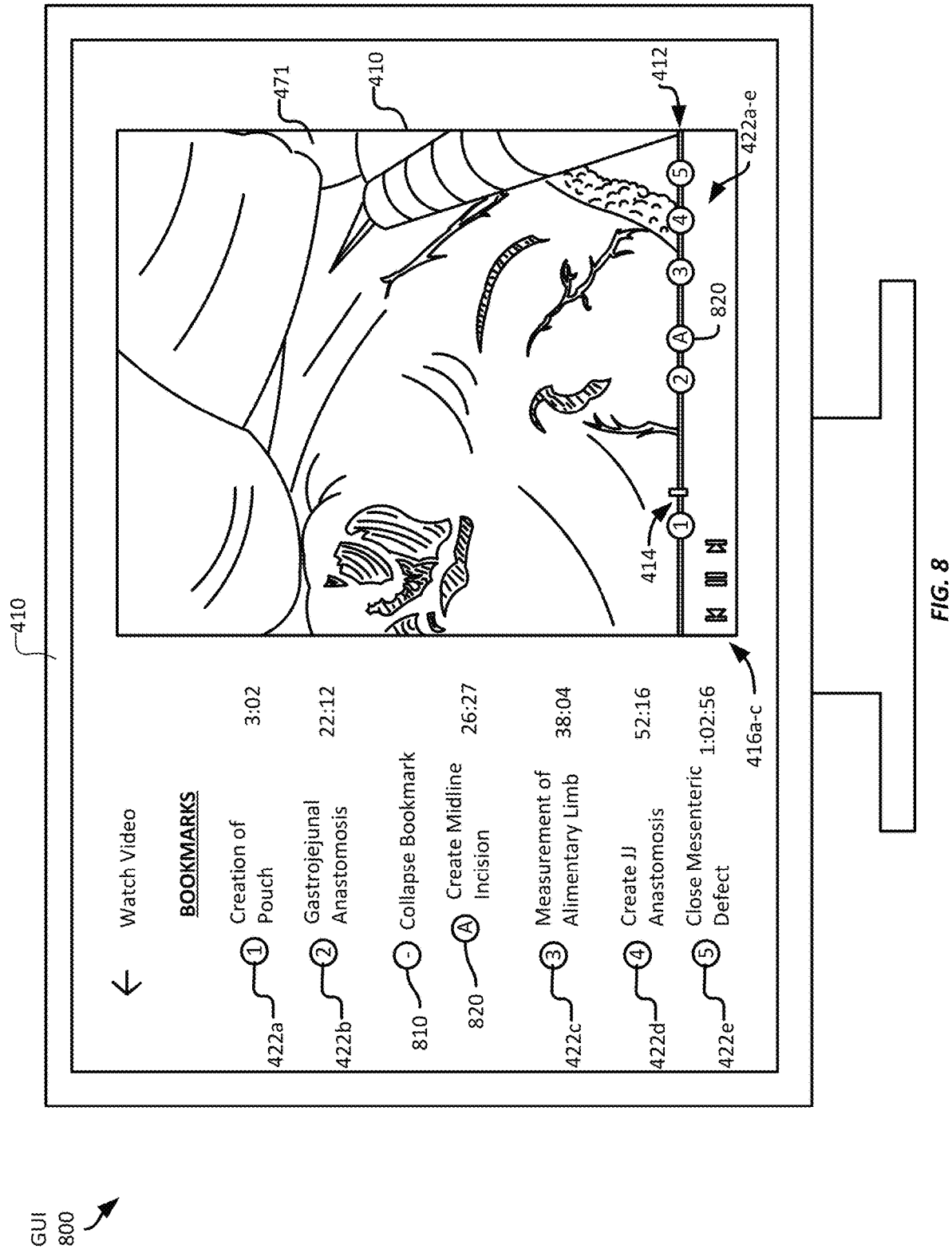
FIGS. 8, 9A-9B, and 10A-10B show example graphical user interfaces for segmenting surgical videos.

As discussed above, after the video has been received by the computing device 107, one or more frames are supplied to an ML technique to determine a surgical procedure type or to identify steps, sub-steps, or events within a surgical procedure. The ML technique(s) thus may apply one or more annotations to the video, such as bookmarks. Thus, when a user first accesses a surgical video using the GUI 500, bookmarks (such as bookmarks 422a-e) may be pre-populated and immediately available for customization or use by the user. In this example, the ML technique created four bookmarks 422a-d and recognized the video 471 as a gastric bypass surgery. In addition, the ML technique recognized the steps corresponding to each of the four bookmarks 422a-d and inserted step names for each, which are visible in the bookmark editor window 520. The user has also selected an option to add a new bookmark and created a new bookmark 422e. The GUI 400 then presents the user with the option to enter a name of the step, sub-step, or event corresponding to the new bookmark 422e, and the user will enter the step name as "Close Mesenteric Defect" (as shown in FIG. 8). The user may also edit the time corresponding to any of the bookmarks by selecting the corresponding timestamp and entering a new time.

While the GUI 500 provides the bookmark editor window 520 to allow the user to create, delete, and modify bookmarks. The user may also directly interact with the bookmarks 422a-e within the video window 410 in any of the example GUIs described with respect to this detailed description. For example, the user may select a bookmark, such as by touching the bookmark or moving a mouse cursor over the bookmark and clicking a button, to jump to the bookmarked frame of the video 471. The user may also edit the position of the bookmark by selecting and dragging the bookmark to a new location along the timeline 412. In some examples, dragging a bookmark may also scrub the video so the user receives immediate feedback to the movement of the bookmark, though such a feature may not be employed in some examples (or may be optionally enabled or disabled by the user). Once the user has finished editing bookmarks, she may save the revisions by returning to the GUI 400 shown in FIG. 4.

In this example, the system 100 saves the bookmarks as metadata associated with the surgical video file(s). Saving the bookmarks may be initiated by an explicit user command, such as by pressing a "Save" button, or the system 100 may auto-save changes to existing bookmarks as the user edits them, while still allowing the user to undo any undesired edits.

Referring now to FIG. 6, FIG. 6 shows example metadata 600 associated with the surgical video 471 shown in FIG. 4-5. The metadata 600 may be stored within one or more of the surgical video files or may be stored as a separate file associated with the surgical video files. The association may be generated or maintained by a filename of the companion metadata file, e.g., by using the same filename as the associated video file but having a different extension. For example, if the video file for a surgical video is called surgery_video.mp4, the metadata file may be named surgery_video.book to indicate the file is a bookmark file. In some examples, the association may be generated or maintained by including the name of the associated video file(s) within the metadata itself, such as is shown in FIG. 6.

In this example, the metadata 600 has been created using a markup language. The annotations are established within a tag, "video_annotations," and includes a number of different tags with associated metadata. The video associated with the annotations is identified by the <video> tag 610. In this case, the associated video is identified by filename; however in some examples, it may be identified by a full path and filename, or by other identifying information, such as a uniform resource locator ("URL"), an identification number, etc.

In addition to the associated video file, the metadata 600 includes information identifying the type and subtype of the video 612 as well as certain other information, such as the title of the video, the name(s) of the surgeon(s), the date and time of the surgery, etc. Such information may be used to index the video file for later searching or to present as information about the video when the video is played, such as in the GUIs 400,500 shown in FIG. 4-5. For example, referring again to FIG. 4, the bibliographic information 420 provides some of the information extracted from the metadata, including the title, the surgeon's name, the date of the surgery, and the time of the surgery. The remaining metadata has been ingested, but may not be explicitly displayed within. For example, the type and subtype information 612 has been parsed and ingested, but is not displayed within the GUI 400, though it may be used to auto-populate one or more search fields if the user elects to perform a search for other surgical videos.

Referring again to FIG. 6, in addition to the information discussed above, the metadata 600 includes metadata describing five bookmarks 622a-622e, which correspond to the bookmarks 422a-e shown in the example GUIs 400,500 shown in FIGS. 4 and 5. As can be seen, each bookmark is established by a <bookmark> </bookmark> tag pair. Each bookmark includes information defining the respective bookmark. For example, bookmark 622a includes four tags: a "step" tag 624, a "name" tag 625, a "begin" tag 626, and an "end" tag 627.

The "step" tag 624, in this example, represents the step of the surgical procedure shown in the video. The "step" tag itself has a preset standardized value defined for the particular step of a Gastric Bypass-type surgery. Thus, the system 100 includes different standardized surgery types, e.g., Gastric_Bypass, which have associated standardized steps, e.g., Bypass_Pouch_Create. Thus, when a new bookmark is created for a Gastric_Bypass surgical video, the user or the system 100 may select one of the standardized steps to associate with a bookmark. Such standardization enables consistent identification of surgical videos and steps within surgical videos, and may enable consistent search results.

It should be appreciated that the "step" tag is an optional tag within the bookmark metadata. Bookmarks may be created arbitrarily at any point in a video and need not be tied to a specific step, though it may be desirable in some examples to restrict bookmarks only to standardized steps, sub-steps, or events. Further, other types of tags may be employed, such as <sub-step> or <event> tags, as mentioned above. Such tags may be used instead of the "step" tag to identify a sub-step or event associated with the respective bookmark. And while in this example, the system 100 employs standardized surgery types and subtypes, steps, sub-steps, and events, in some examples, any or all of these tags may include user-defined information that may or may not be standardized for some or all users.

Referring again to bookmark 622a, the bookmark 622a also includes "name," "begin," and "end" tags, which include further information regarding the bookmark 622a. The "name" tag in this example stores the name of the bookmark, which may be displayed in the GUI 400,500. For example, the user may hover a cursor over the bookmark 422a or may press and hold on the bookmark 422a, which may cause the GUI 400,500 to display the information stored in the "name" tag. Alternatively, the user may be presented with a list of bookmarks available within a surgical video, which may include the respective names of each displayed bookmark.

The "begin" and "end" tags include timestamps within the video and may be used to identify specific frames in the video 471 associated with the bookmark. The "begin" tag 626 indicates the location of the bookmark 622*a* within the video 471 and the location to display a visual indicator of the bookmark 422*a* on a video timeline 412. Thus, if the user adjusts the location of the bookmark, it may change the value stored by the "begin" tag. While the begin tag in this example specifies a video frame using minutes and seconds, other formats may be used. For example, the begin tag may specific a frame number using an (hours):minutes:seconds.frame. For example, if the video is recorded at 24 frames per second, the "begin" tag may be represented as 3:02.14 indicating the 15$^{th}$ frame after the 3:02 mark in the video, where the frames are numbered 0 to 23. Still other frame numbering conventions may be employed according to different examples.

The "end" tag represents the end of a video segment associated with the bookmark 622*a*. Thus, a bookmark may represent a single frame or a segment of video according to some examples. The "end" tag may be employed if a bookmark has further embedded bookmarks. For example, bookmarks may be established in a hierarchy such as to identify a step, one or more sub-steps of the step, or one or more events occurring during the step. Thus, an "end" tag may explicitly indicate the end of the step, while additional child bookmarks may be defined within the video segment established by the bookmark. Alternatively, one video segment may end by default when another bookmark at the same hierarchical level is reached, in some examples.

Figure 7:
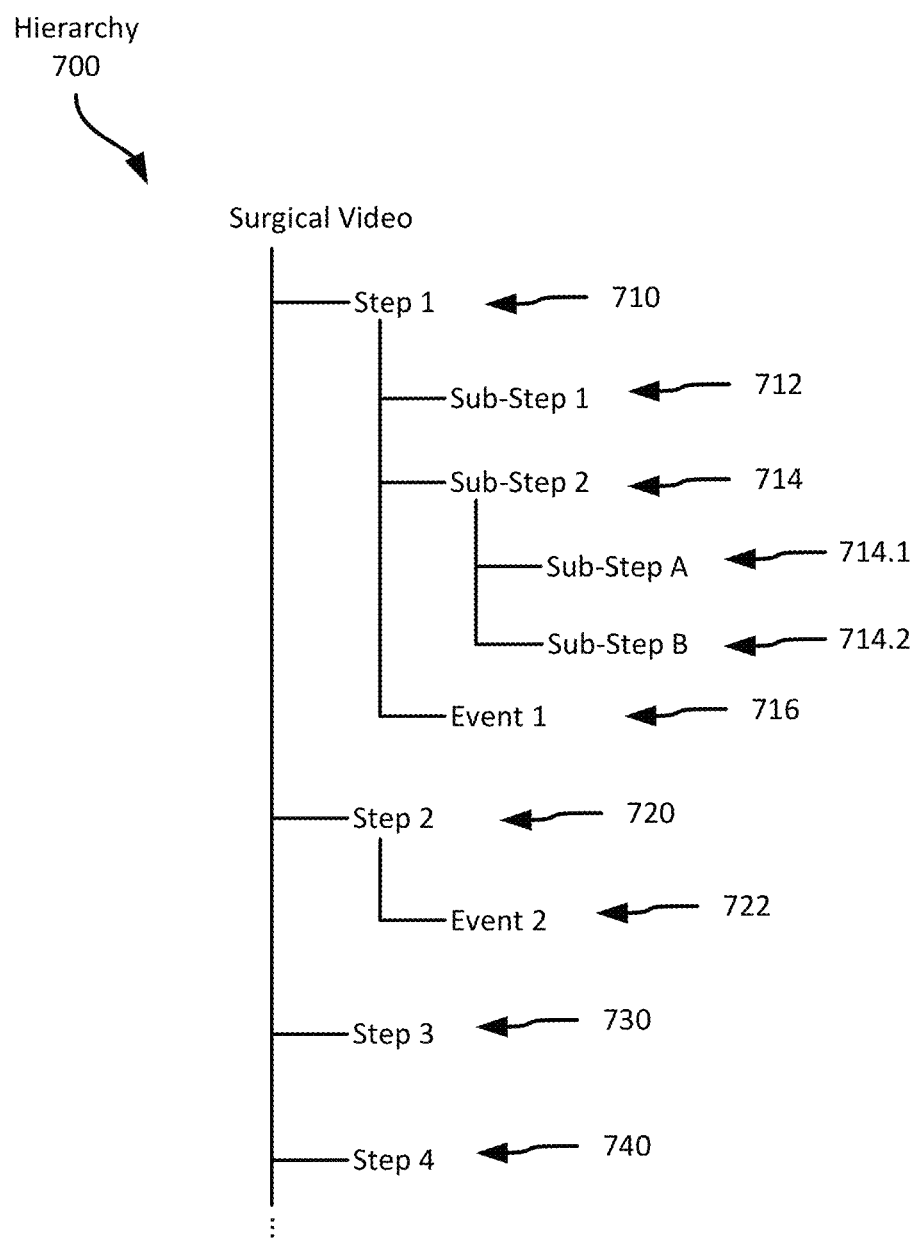
FIG. 7 shows example hierarchical bookmark information for segmenting surgical videos.

Referring now to FIG. 7, FIG. 7 shows an example bookmark hierarchy 700 for a surgical video according to one example. In this example, the hierarchy begins at the surgical video, which has four steps 710-740. Step 1 (710) has two sub-steps 712, 714 and an event 716. Further, sub-step 2 (714) has two further sub-steps 714.1-714.2. Similarly step 2 (720) has an associated event 722. Steps 3-4 (730-740) do not have any sub-steps. Such sub-steps and events may be represented using metadata similar to the excerpt below:

```
<bookmark>
 <step>Step 1</step>
 <begin>10:00</begin>
 <end>30:00</end>
 <bookmark>
  <step>Sub-Step 1</step>
  <begin>11:15</begin>
  <end>13:30</end>
 </bookmark>
 <bookmark>
  <step>Sub-Step 2</step>
  <begin>13:30</begin>
  <end>16:00</end>
  <bookmark>
   <step>Sub-Step A</step>
   <begin>14:00</begin>
   <end>15:00</end>
  </bookmark>
  <bookmark>
   <step>Sub-Step B</step>
   <begin>15:00</begin>
   <end>16:00</end>
  </bookmark>
 </bookmark>
<bookmark>
```
-continued
```
 <step>Event 1</step>
 <begin>17:45</begin>
 </bookmark>
</bookmark>
```

Employing such hierarchical bookmarks may enable richer annotations of surgical videos and easier navigation to segments of interest within the videos. Further, hierarchical bookmarks may allow collapsing and expanding of bookmarks on a video's timeline or in a companion navigation window.

For example, referring to FIG. 8, FIG. 8 shows an example GUI 800 for segmenting surgical videos. In this example, the GUI 800 provides playback functionality for surgical videos. The GUI 800 provides the video window 410 shown in FIG. 4 with playback controls 416*a-c*. In addition, like the example GUI 400 shown in FIG. 4, the video timeline 412 includes multiple bookmarks 422*a-e*, 820 that a user may select to jump immediately to a particular frame in the video 471. For example, a user may touch (using a touch-sensitive input device), or move a cursor over and select, one of the bookmark icons 422*a-e* (each a circle with a number or letter) to immediately jump the playback cursor 414 to the video frame corresponding to the bookmark.

Alternatively, the user may select one or more of the bookmarks from the list of bookmarks shown to the left of the video window 410. In this example, each bookmark 422*a-e* is listed and includes a corresponding description of the bookmark as well as the corresponding timestamp within the video. A user may select any of the bookmarks in the list to jump to the corresponding frame of the video 471. Alternatively, the user may select multiple bookmarks, such as by holding CTRL while selecting bookmarks, and then may continuously play surgical video beginning with the first (temporal) bookmark and then proceed seamlessly to the next bookmark, even if that would involve skipping over a segment of video. For example, if a user selects bookmarks 1, 3, and 4 (422*a, c, d*), and presses 'Play," the video window 410 may present the video beginning at the frame corresponding to bookmark 1 (422*a*) and, upon reaching bookmark 2 (422*b*), may skip to bookmark 3 (422*c*) and continue playing through to the end of bookmark 4 (422*d*), at which time the video may stop, or may restart again at bookmark 1 (422*a*).

In addition, because bookmark 422*b* has a nested bookmark 'A' (820), the GUI 800 provides the option 810 to expand or collapse the bookmark list to show or hide such nested bookmarks. When the bookmark list, or part of the bookmark list, is collapsed, only the top-level bookmarks 422*a-e* are shown in the list and on the timeline along with corresponding option 810 to expand nested bookmarks 820 for a respective top-level bookmark 422*a-e*. It should be appreciated that any or all of the top-level bookmarks 422*a-e* may have nested bookmarks according to a hierarchy, each of which may be independently expanded or collapsed (or globally expanded or collapsed in some examples). Alternatively, a user may access an expand/collapse option on the timeline for a particular bookmark, e.g., bookmark 422*b*, to display or hide its nested bookmarks, e.g., bookmark 820. For example, a user may touch and hold on a bookmark to access such an option, or the user may right-click on the bookmark to obtain a context-sensitive menu having such options. Thus, a bookmark hierarchy may be represented by metadata as shown in FIG. 7 and may be accessed in a number of different ways, including through the use of expanding/collapsing bookmark listings as shown in the example GUI 800 in FIG. 8.

Referring again to FIG. 6, tags that lack a value are not represented within the metadata, such as in bookmark 622*e*. Bookmark 622*e* only includes a "begin" tag but no corresponding "step," "name," or "end" tag as are present in the other bookmarks 622*a-d*. In this example, the system 100 reads the metadata and ingests the bookmark as having a "begin" timestamp of 1:02:56, but will not identify any corresponding standardized step or any name associated with the bookmark. In some examples, a user may be presented with options to enter data for each such field, which may then be stored in the metadata using the appropriate tag. In some examples, however, tags without values may still be present in the metadata, but with no data. For example, bookmark 622*e* may be represented as follows in some examples:

<bookmark>
  <step> </step>
  <name> </name>
  <begin>1:02:56</begin>
  <end> </end>
</bookmark>

While only certain types of metadata are shown in FIG. 6, it should be appreciated that any suitable metadata may be employed according to different examples. For example, other information such as user-provided annotations, e.g., notes, comments, scoring information, etc., may be stored in metadata. Referring again to FIG. 5, a user may select the "add new bookmark" option to add a new bookmark at a point in the video and enter commentary or feedback into the bookmark in a "notes" field. Such information may then be stored in the metadata within a <note> </note> or <comment> </comment> tag associated with the bookmark. Further other types of information, such as hyperlinks (e.g., a <link> </link> tag) to another video (or video bookmark) that may provide a comparison to the displayed video 471, e.g., a particularly good or bad example of the step of the surgical procedure. Still other type of information may be stored in the metadata according to different examples or design parameters.

Figure 9A:
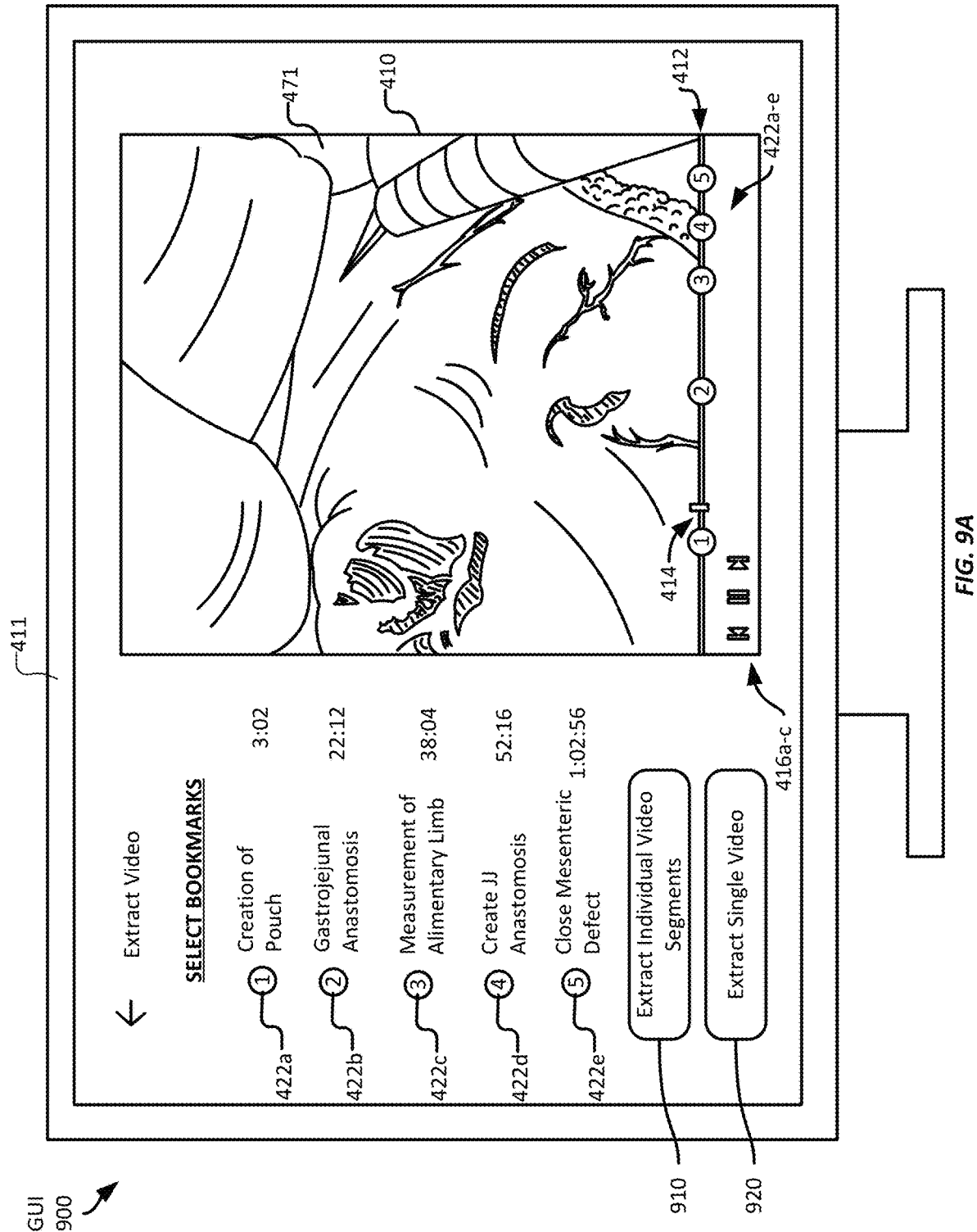

Referring now to FIG. 9A, FIG. 9A shows an example GUI 900 to allow the user to extract one or more video segments from a surgical video. This example GUI 900 includes the video window 400 described above with respect to FIG. 4 and provides a list of the bookmarks associated with the surgical video 471. As discussed above, an identifier is positioned on the video timeline 412 for each of the bookmarks 422*a-e* listed.

As discussed above, surgical videos can run several hours in length. Thus, to review only a specific portion of the video 471, a user may manually scrub through the video to find the interesting portion of video. Such a process is tedious and may limit the usefulness of such surgical videos. To help address this issue, systems and methods according to this disclosure enable a user to extract specific video segments efficiently by using bookmarks associated with the surgical video 471. As discussed above, the bookmarks may be initially created by one or more ML techniques based on recognizing the type of surgery and individual steps of the surgery, and the user may later adjust the bookmarks, add new ones, or delete existing ones. Once the bookmarks 422*a-e* have been established and associated with the video 471, the GUI 900 enables the user to employ the bookmarks to select video segments and extract those segments as discrete surgical videos. To extract one or more video segments using this example GUI 900, the user selects one or more bookmarks 422*a-e* and selects an option to either "extract individual video segments" 910 or to "extract [a] single video" 920.

While this example GUI 900 illustrates using bookmarks specifically, it should be appreciated that some examples may not require the use of bookmarks to establish one or more segments of video. Rather, some examples, may allow the user to select no bookmarks and select an option to extract a video segment. The user may then specify any arbitrary start and end points within the video to create a video segment. The computing device may then extract a video segment based on the supplied start and end points. If the user specifies multiple start and end points, the computing device may then extract video segments for each pair of start and end points. Further, any start may also operate as an end point for previous segment. Likewise, any end point may also operate as a start point for a subsequent segment. The computing device may further allow the user to also establish either or both of the start and end points as a bookmark into the source video.

Figure 9B:
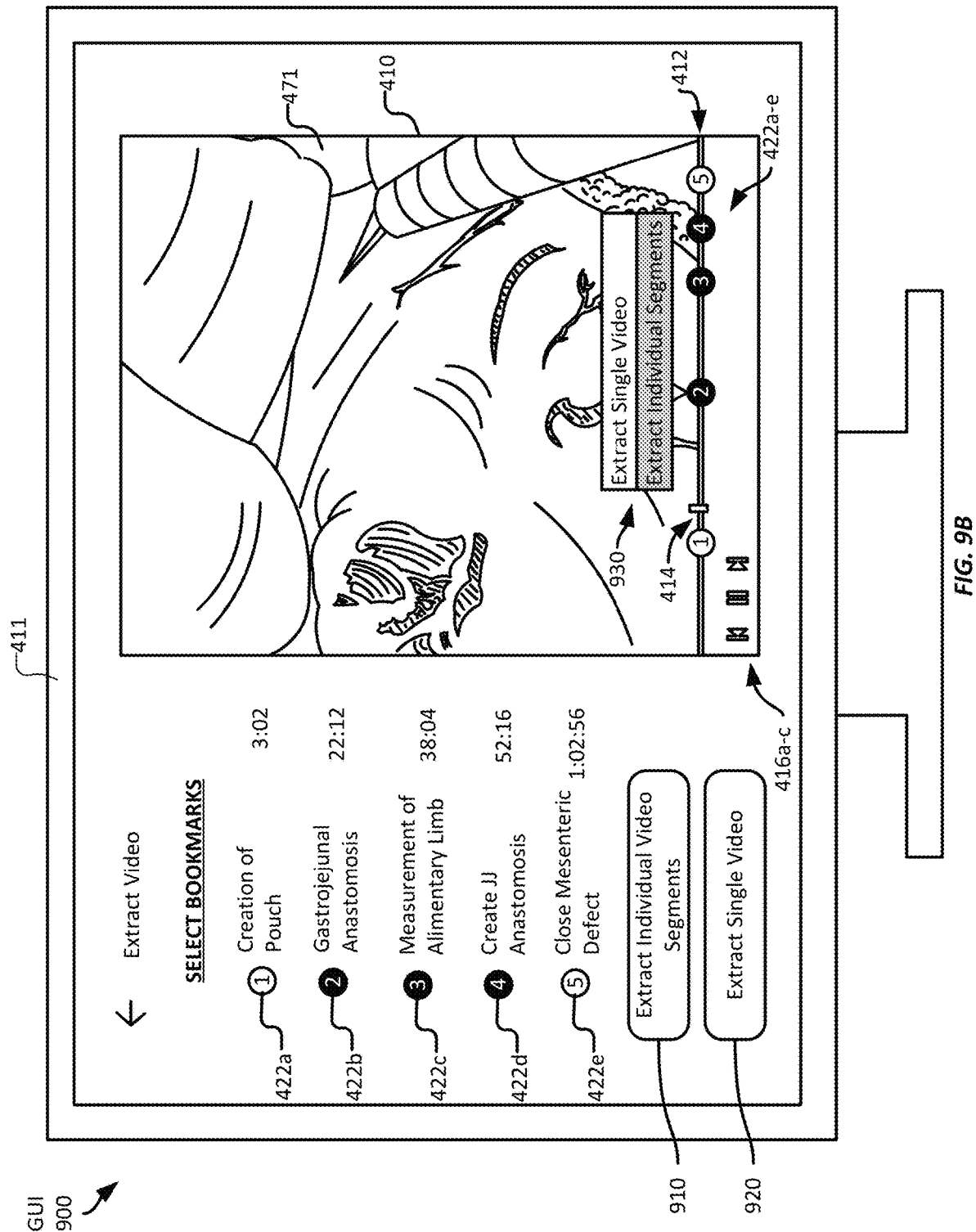

Referring now to FIG. 9B, FIG. 9B shows the GUI 900 where a user has selected three bookmarks 422*b-d*. After selecting the bookmarks, the user selects one of the two extraction options 910, 920 to extract one or more video segments. Alternatively, the user can open a context-sensitive menu 930, such as by right-clicking on a bookmark 422*b* within the timeline 412 or touching and holding on the bookmark 422*b*, and select the desired option 910, 920 from the menu. In this example, if the user selects the "extract individual video segments" option 910, the system 100 will generate two new video files. The first video file will include video frames beginning at bookmark 2 (422*b*) and ending at bookmark 3 (422*c*), while the second video file will include video frames beginning at bookmark 3 (422*c*) and ending at bookmark 4 (422*d*). Each new video file will be given a default filename based on the name of the surgical video 471 and including the name of the bookmark marking the beginning of the video. For example, the surgical video 471 has the filename "GastricBypass_DrSamBrown_141120171630.mp4." Thus, the first video file may be assigned the filename "gastrojejunal_anastomosis_GastricBypass_DrSamBrown_141120171630.mp4." The second video file may be assigned a filename according to the same convention.

In this example, extracting the video also includes generating metadata for the extracted video files, which may include creating new metadata or copying corresponding metadata from the surgical video's metadata, and associating the new metadata with the extracted video. For example, the first video file may include information copied from the metadata 600 shown in FIG. 6, such as the <type>, <subtype>, <surgeon>, <date>, and <time> tags, but the <video> tags may include the filename of the respective extracted video file, and the <title> tag may include information based on the extracted video, e.g., the name of the initial bookmark 422*b*: <title>Gastrojejunal Anastomosis—Gastric Bypass—High BMI</title>. Copied metadata may include bookmark information for nested bookmarks according a hierarchical bookmarking scheme. Such copying may preserve any bookmarks embedded within the extracted segment(s) of the surgical video 471.

Alternatively to selecting the "extract individual video segments" option 910, the user may select the "extract single video" option 920. In this example, such a selection would cause the system 100 to generate a single video file including all video frames beginning at bookmark 422*b* and ending at bookmark 422d. If non-consecutive bookmarks are selected, e.g., 422a, 422c, and 422d, some example systems may extract video frames between bookmark 422a and 422b as well as between 422c and 422d and store them in a single video file. Or some examples may treat each selected bookmark as a selected segment, thus selecting bookmarks 422a, 422c, and 422d may cause some systems to extract all frames between bookmarks 422a-422b, 422c-422d, and 422d-422e. Still further variations may be employed according to different examples. The system 100 then also extracts the video frames to a single file and also creates metadata associated with the extracted video generally as discussed above with respect to the "extract individual video segments" option 910. The newly created video file may include the filename of the surgical video 471 as well as indicators of the bookmarks employed to create the video file, such as discussed above.

Thus, employing example GUIs, such as the example shown in FIGS. 9A-9B, a user may easily extract one or more video segments from a surgical video 471. Such functionality may reduce the burden on a surgeon when later reviewing the surgery because the surgeon may immediately access a short video clip rather than the entire surgical video 471. Further, the surgeon may be able to more easily obtain or share a copy of a video segment, which is likely significantly smaller in size than the full surgical video 471.

It should be appreciated that the specific GUI 900 and techniques discussed according to this example may be implemented in different ways with different graphical features or interface elements; however, such examples all enable the user to easily select relevant portions of the video and extract them to one or more files.

Figure 10A:
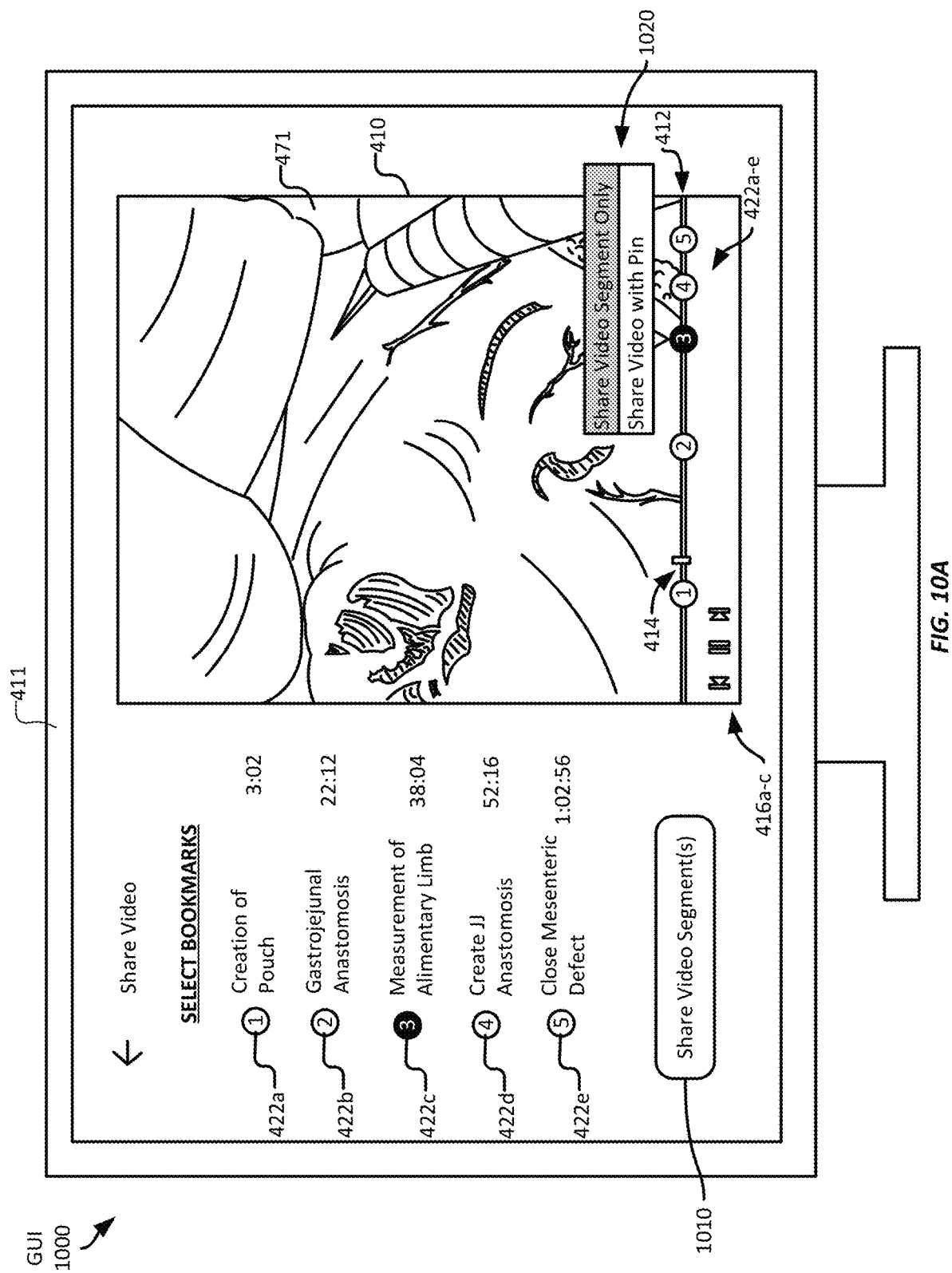
Figure 10B:
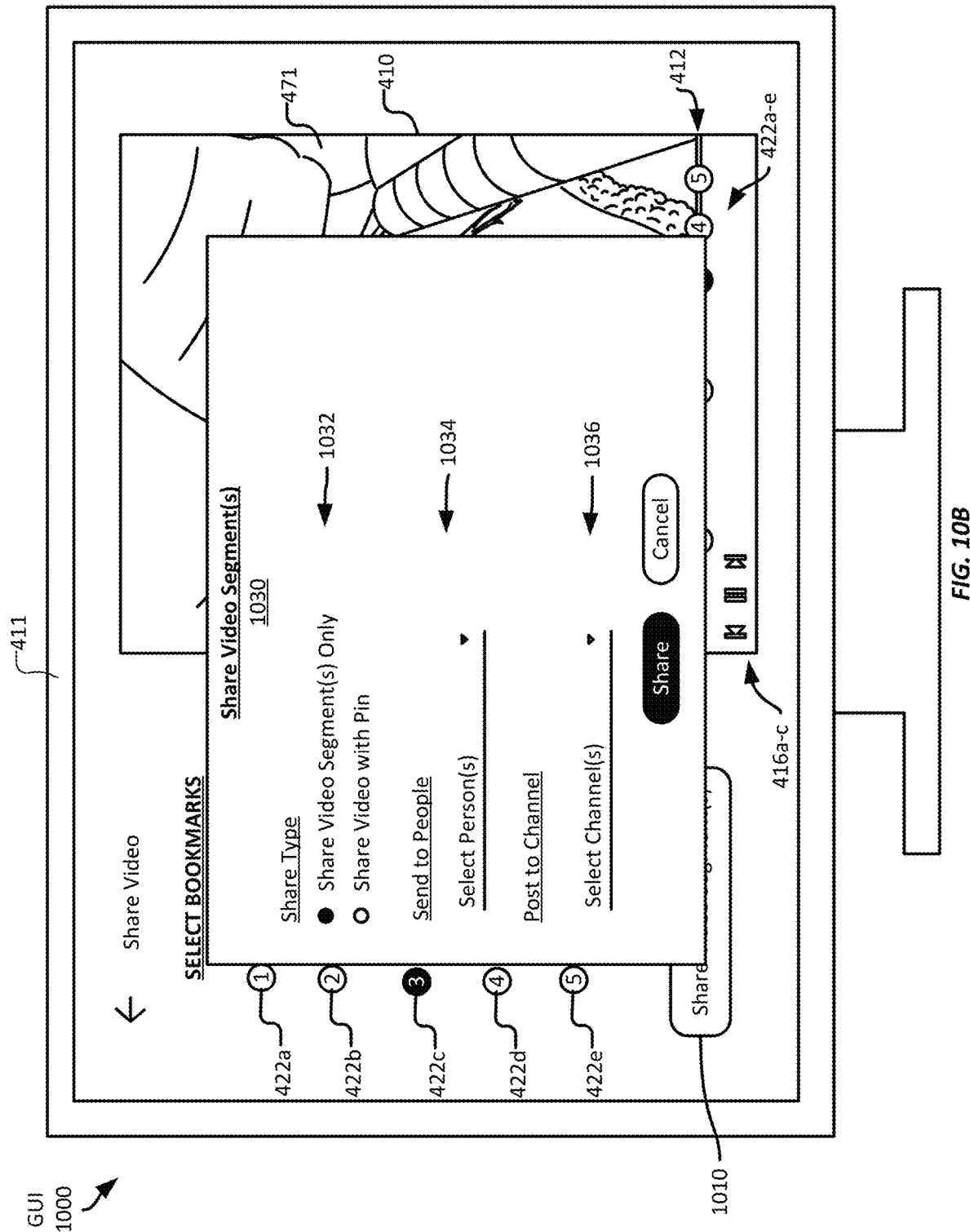

Referring now to FIGS. 10A-10B, FIG. 10A shows an example GUI 1000 that enables users to share segments of surgical videos with others. In this example, the GUI 1000 presents the user with a video window 410 showing a surgical video 471, as discussed above with respect to FIG. 4. In addition, the GUI 1000 shows the bookmarks 422a-e established for the video.

To share one or more video segments, the user selects one or more bookmarks 422a-e in the video and selects the "Share Video Segments" button 1010, or the user may right-click (or touch and hold, etc.) to open a context-sensitive menu with two options: sharing a video segment only, or sharing the video with pin. In this example, the user has selected bookmark 422c and opened the context-sensitive menu 1020 and selected the option to "share video segment only."

Referring now to FIG. 10B, FIG. 10B shows the example GUI 1000, which has opened a dialog window 1030 after the user selected the button 1010. The dialog window 1030, which may be accessed either via the button 1010 or the context-sensitive menu 1020, provides options to the user for sharing a video segment. In this example, the GUI 1000 provides options to select a type of sharing 1032, to select the people 1034 with whom to share the video segment(s), and to select the channel(s) 1036 to which to post the video segment(s).

The "Share Type" options reflect the options from the context-sensitive menu 1020 and an option was selected based on the user's selection in the context-sensitive menu 1020. Had the user selected the button 1010 instead, the "share type" options 1032 would have been presented as unselected, though in some examples, one option may be selected by default.

The two options presented in this example are "share video segment(s) only" and "share video with pin." The "share video segment(s) only" option employs aspects of the video segment extraction functionality discussed above with respect to FIGS. 9A-9B. If a user selects this option, video segments are extracted based on the selected bookmarks, as discussed above, and are then shared with the selected people or channels as will be discussed below. However, if the user selects the "share video with pin," the entire video is shared with the selected people or contacts, along with an indicator at which the video cursor 414 is initially set at the recipient's video player. The recipient may then immediately begin playing the video from the "pinned" location, e.g., at a particular bookmark.

The "Send to People" section provides a drop-down menu from which the user may select one or more people with whom to share the video segment(s). For example, the user may select one or more colleagues, administrators, etc. from a drop-down list of names. The list of names in this example is populated with users registered with the system 100 and authorized to receive surgical videos. Within the drop-down list, the user may select each name with whom to share the video segment(s). In some examples, the GUI 1000 may also allow the user to enter user information, such as an email address, username, or user identification number, to identify people with whom to share the video segment(s). Such fields may also provide auto-complete functionality to allow the system to present recipient options as the user enters information into the field.

In addition to sharing the video people, or instead of, the GUI 1000 provides the option to post the video segment(s) to one or more channels. For example, a surgical center may provide one or more online channels its surgeons and staff can access while at work to post or review information prior to an upcoming surgery, post comments or questions, etc. In addition, the channels may allow the user to post video content for review or comment from others at the surgical center. Alternatively, the channels may include video channels on social media sites, such as YouTube®, which may be directly accessed by the system 100 to upload one or more video segments. The channels may be accessed in a drop-down list of available channels. The user may also, in some examples, provide access information for one or more channels, such as by providing login information for, e.g., a YouTube® account, which may then provide a list of the user's YouTube® channel. Still other types of channels may be selected according to different examples.

After selecting the "share type" option 1032 and one or more recipients, whether people or channels, the user may select the "Share" button to share the selected video segment(s). If the user changes her mind, however, she may "Cancel" the sharing operation and return to the main screen of the GUI 1000 shown in FIG. 10A.

Figure 11:
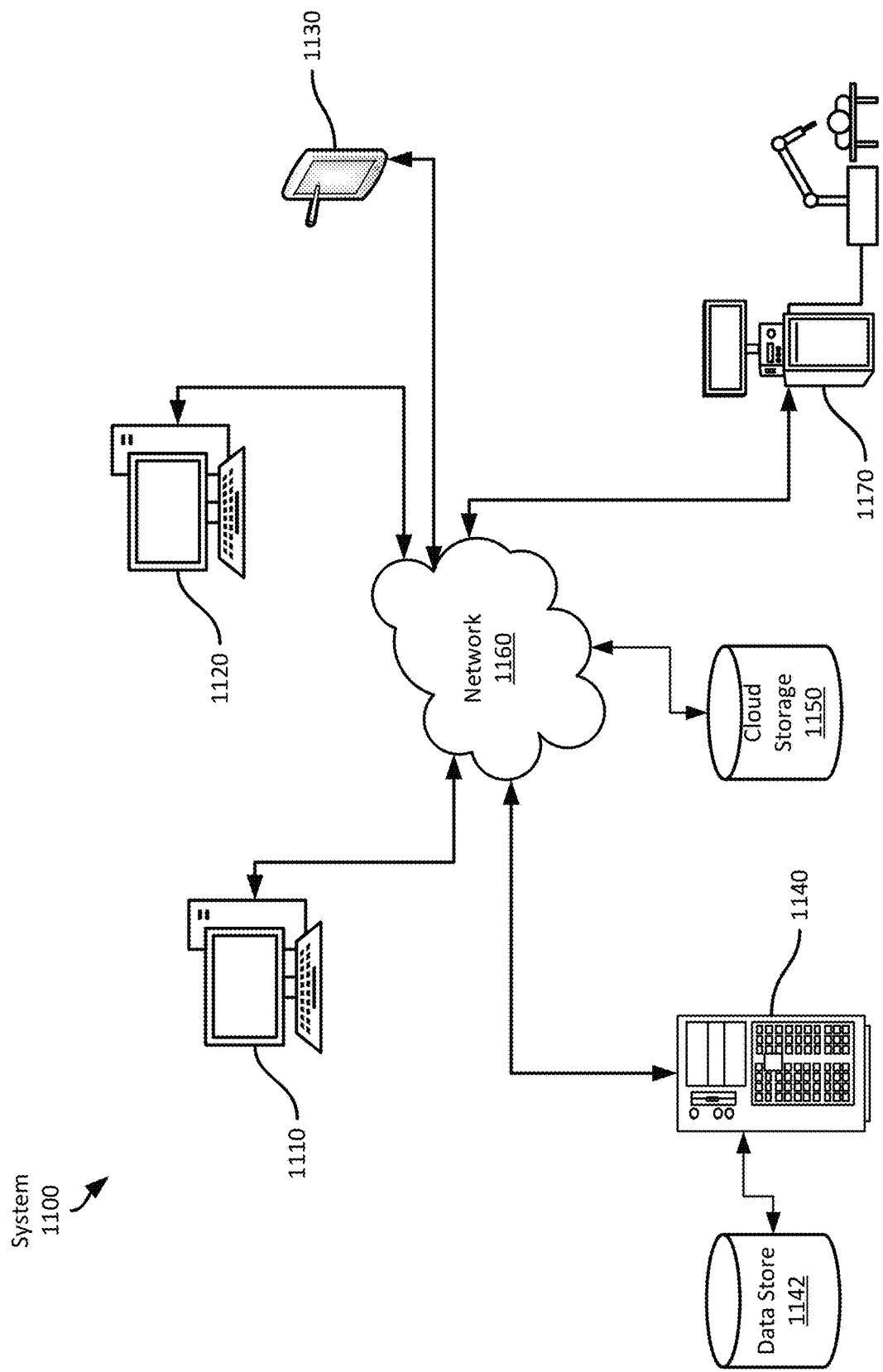
FIG. 11 shows an example system for segmenting surgical videos.

Referring now to FIG. 11, FIG. 11 shows an example system 1100 for segmenting surgical videos. The system 1100 shown in FIG. 11 may be suitable to enable sharing videos as discussed above with respect to FIGS. 10A-10B, though any suitable system according to this disclosure may be employed. The system 1100 includes two user stations 1100, 1120 and a mobile device 1130 that are in communication with server 1140 via network 1160. In this example, the network 1160 is the internet, but may be any suitable network or combination of networks according to different examples. The server 1140 has access to local data store 1142. A surgical robot 1170 is connected to the server 1140 as well via network 1160. In addition, server 1140, as well as user stations 1110, 1120, mobile device 1130, and the surgical robot 1170, has access to cloud storage 1150 via the network 1160. The surgical robot 1170 may upload surgical videos to the server 1140 or to cloud storage 1150 during or following surgical procedures. The uploaded surgical videos may be processed at the server 1140 as discussed above to provide initial bookmarks and metadata, and then stored in the data store 1142.

After a new surgical video has been processed and stored in the data store 1142, the surgical team may be notified that the video has been processed and is available for access. For example, the system 1100 may email each member of the surgical team, or it may generate a message available via a web portal application indicating a new surgical video is available. At a later time, one of the surgical team members may access the video via the portal, such as by interacting with one or more of the example GUIs described herein, using a user station 1110 or a mobile device 1130. The user may then access the video, select one or more video segments to share, and select another user to share the video, such as described above.

The sharing command may be sent to the server 1140 via the GUI and the server 1140 may generate one or more new videos based on the selected video segments and store them in the data store 1142 or cloud storage 1150, if that option was selected. Otherwise, the server 1140 may generate a message to each identified recipient indicating that the video(s) have been shared with him or her, and transmit the message, e.g., via email or via a messaging feature in the web portal application. Alternatively, the server 1140 may add the shared video(s) to a list of shared videos in the user's web portal account. The recipient(s) may then access the web portal via another user station, e.g., user station 1120, and access the shared videos. Thus, the networked example system 1100 may provide sharing capabilities amongst various users of the system 1100 and may also interact with the surgical robot 1170 to obtain new surgical videos from time to time.

Figure 12A:
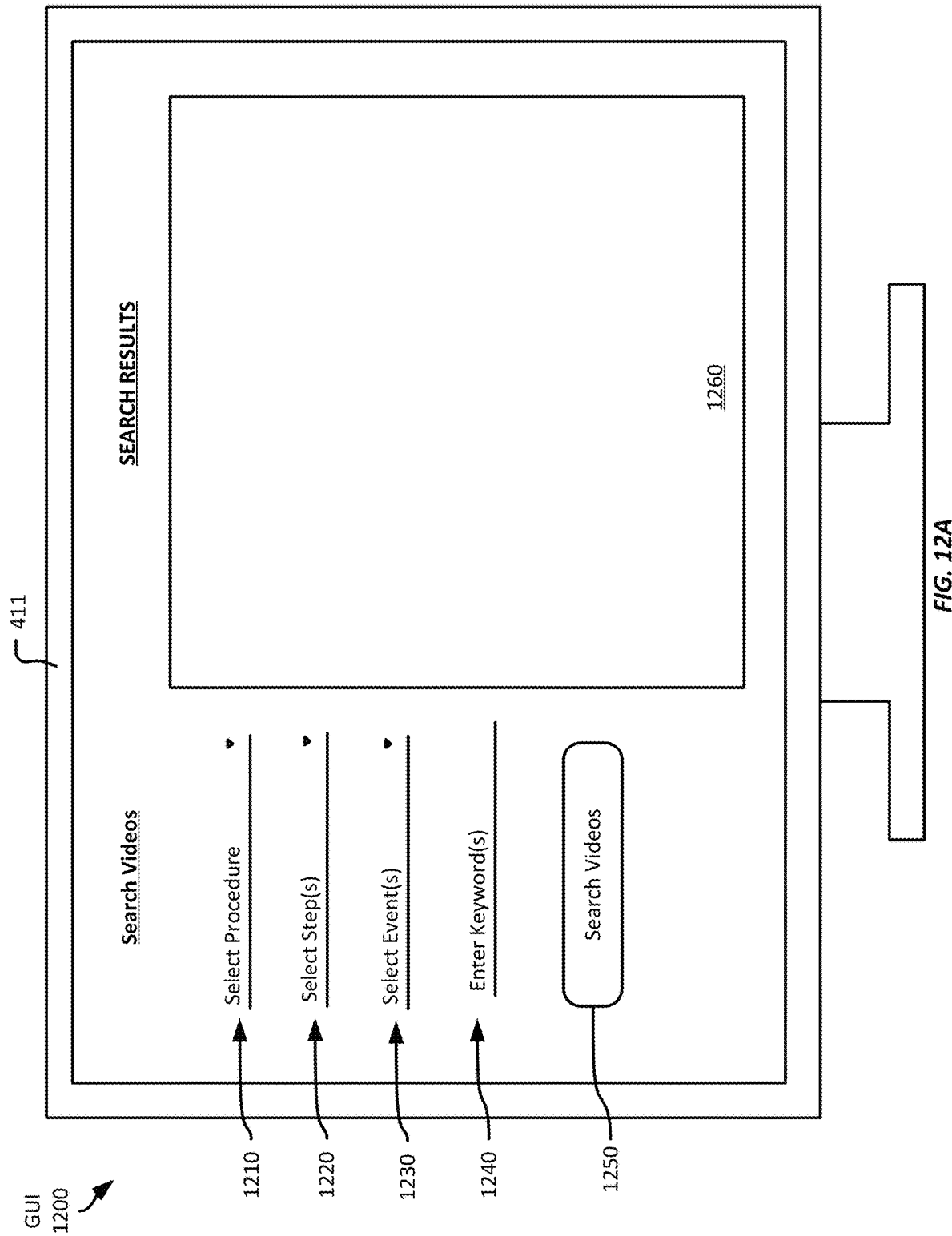
FIGS. 12A-12B show example graphical user interfaces for searching for surgical videos.

Referring now to FIG. 12A, FIG. 12A shows an example GUI 1200 to search for videos in a system for segmenting surgical videos. This example GUI 1200 enables a user to search for one or more surgical videos based on bookmarks associated with the videos. In this example, the GUI 1200 provides drop-down lists 1210-1230 to allow a user to select one or more surgical procedure types 1210, one or more steps of a surgical procedure 1220, or one or more events 1230. The drop-down lists 1210-1230 are populated with the standardized surgical procedure names, steps, and events, respectively, though in some examples, user-created bookmarks may also be provided. For example, if a user adds a bookmark to a surgical video and enters a customized name, not a standardized step or event, the system 100 may add the customized name to the list of steps 1220 or the list of events 1230, as appropriate, that may be searched. In some examples; however, the standardized steps or events are not modified. Instead, a user may search for such customized names using the keyword search area 1240. Alternatively, the user may enter one or more keywords into the keyword search area 1240 that may match to metadata associated with one or more surgical videos. Such keywords may include video titles, surgeon names, dates, times, medical centers, patient identification numbers, etc.

After the user has entered one or more search parameters, such as a surgical procedure, a surgical step, an event, or a keyword, the "search videos" button 1250 may be enabled and the user may press the button to initiate a search. Search results may then be presented in the search window 1260 for the user to review and select.

Figure 12B:
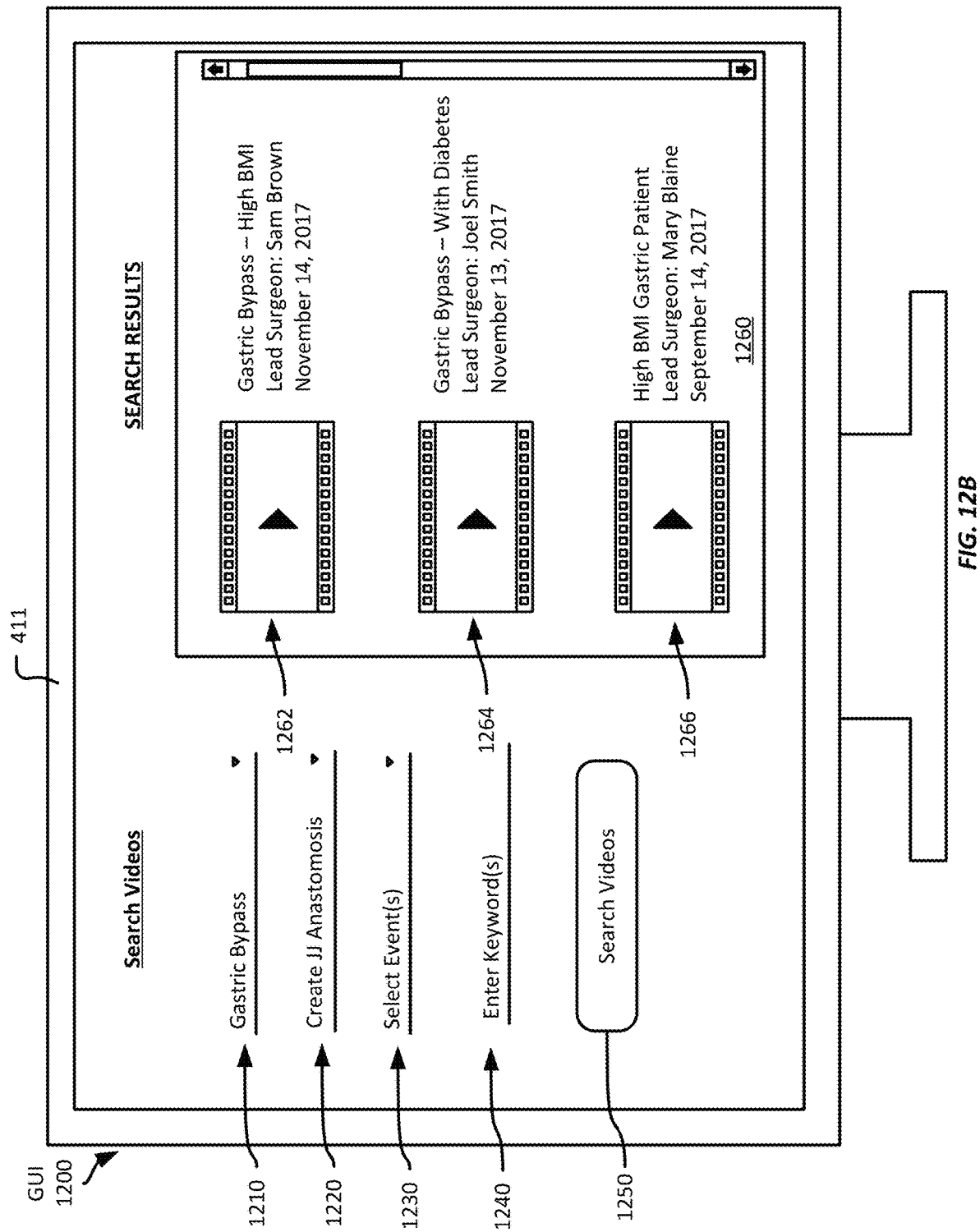

Referring now to FIG. 12B, FIG. 12B shows the example GUI 1200 after the user has entered search parameters and pressed the "search videos" button 1250. In this example, the user has selected "Gastric Bypass" as the surgery type, and "Create JJ Anastomosis" as the surgical step. She did not select any events or enter any keywords to search. The system 100 executed a search on data storage 133 to identify any surgical videos with metadata indicating "Gastric Bypass" as the surgery type and with a surgical step identified as "Create JJ Anastomosis." Thus, in this example, the data store 133 indexes the surgical videos based at least in part on their respective associated metadata. The surgical videos 1262-1266 that satisfy the search criteria are then presented within the search window 1260.

The search window 1260 in this example presents representations of each identified video and some bibliographic information about each. In this example, the bibliographic information is obtained from the metadata associated with the respective surgical video and the displayed bibliographic information includes the title of the respective video, the lead surgeon for the surgical procedure, and the date of the surgery. Other example systems 100 or GUIs 1200 may provide other bibliographic information, or may provide information indicating a relevance score of the identified video to the search parameters. For example, if a video satisfies some, but not all search parameters, the video may receive a lower relevance score than one that satisfies all search parameters. In one example, a relevance sore may be calculated by determining the total number of search parameters and dividing that value into the number of search parameters for a surgical video that match the search parameters. For example, if a search includes four search parameters, and a surgical video matches three of the search parameters, the surgical video may have a relevance score of 75%. Still other techniques may be employed that weight one or more search parameters more or less than others.

After the results of the search have been presented in the search window 1260, the user may select one or more of the videos to view. For example, the user may double click on a video to switch to GUI 400 shown in FIG. 4 to interact with the view, such as view the video by selection the "Watch Video" option 460. The user may then return to the search results and select a different video or perform a new search.

Figure 13:
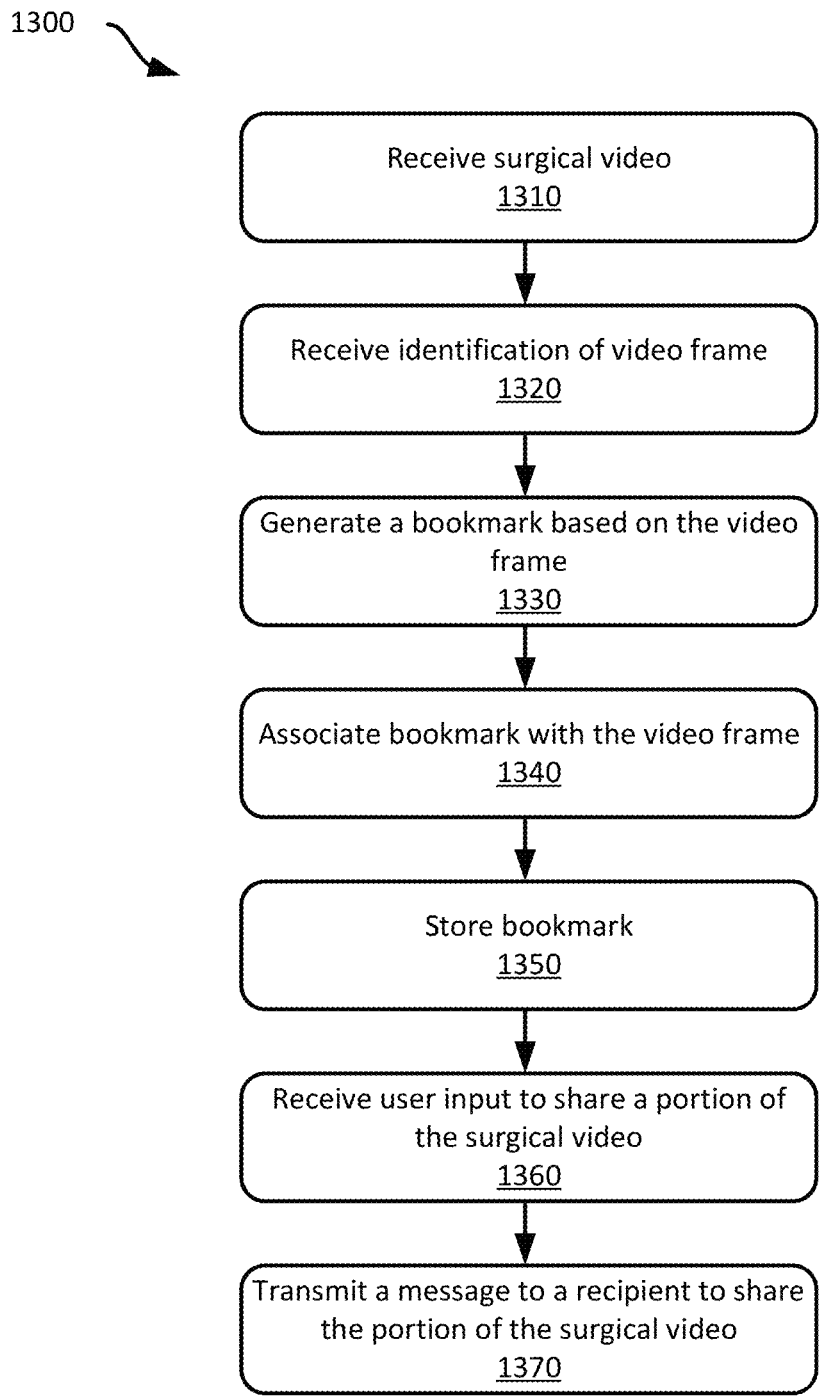
FIGS. 13-14 show example methods for segmenting surgical videos.

Referring now to FIG. 13, FIG. 13 shows an example method 1300 for segmenting surgical videos. This example method 1300 will be described with respect to the example system 100 shown in FIG. 1; however it should be appreciated that any suitable system may be employed, such as the systems shown in FIG. 2, 3A-3B, or 11.

At block 1310, the computing device 107 receives surgical video from the surgical robot 121, which includes a sequence of video frames of a surgical procedure. In this example, the computing device 107 receives video signals from the camera 101 and saves video frames to a video file based on the video signals. The video file is saved to local data store 133 in this example, but in some examples, the video file may be streamed to a remote server or to cloud storage.

While the example above discusses receiving video signals from a surgical robot 121, in some examples, the computing device 107 may receive surgical video by accessing a video file stored in data store 133. For example, after the surgery has concluded, the computing device 107 may retrieve the video file from data store 133. With respect to another system 1100 discussed herein, surgical video may be received by downloading one or more video files from the data store 1142 or cloud storage 1150.

At block 1320, the computing device 107 receives an identification of a video frame within the surgical video. In this example, the computing device 107 provides the received surgical video to one or more ML techniques. For example, the computing device 107 have execute an ML technique trained to recognize a type of a surgical procedure based on frames of video. The computing device 107 may provide part or all of the received surgical video the trained ML technique, which may then provide an indication of the type of the surgical procedure performed in the surgical video. After receiving the type of the surgical procedure, the computing device 107 may then provide the surgical video and the type of the surgical procedure to a second ML technique. The second ML technique may be trained to recognize steps of one or more surgical procedures based on the type of the surgical procedure and the received surgical video. The second ML technique may then process the surgical video and identify one or more frames of the video associated with the beginnings of different steps of the surgical procedure.

For example, referring to the GUI 800 shown in FIG. 8, the computing device 107, after receiving the surgical video 471 from the surgical robot 121, determines that the surgical video 471 is of a gastric bypass by using a first ML technique. The computing device 107 then provides the surgical video to a second ML technique along with an indication that the surgical video is of a gastric bypass surgery. The second ML technique then processes the video and recognizes five steps and one sub-step within the surgical video 471: (step 1) creation of a pouch, (step 2) a gastrojejunal anastomosis, (sub-step A) creation of a midline incision, (step 3) measurement of the alimentary ling, (step 4) creation of the jejuno-jejunal anastomosis, and (step 5) closing the mesenteric defect. The computing device 107 then receives from the second ML technique indications of the recognized steps and frames within the video corresponding to the beginnings of each of the recognized steps:

Step 1 Creation of Pouch 3:02.0
Step 2 Gastrojejunal Anastomosis 22:12.13
Sub-step A Create Midline Incision 26:27.9
Step 3 Measurement of Alimentary Limb 38:04.7
Step 4 Create JJ Anastomosis 52:16.22
Step 5 Close Mesenteric Defect 1:02:56.14

As discussed above, the number following the decimal point indicates which frame within the particular second is specified. This surgical video 471 has a frame rate of 24 frames per second, though any suitable frame rate may be employed. While the example above employs different ML techniques to recognize the type of the surgical procedure and the steps of the surgical procedure, it should be appreciated that a single ML technique may be trained to both recognize the type of the surgical procedure and to recognize the steps of the surgical procedure, as well as sub-steps or events. Thus in some examples, only one ML technique may be employed, though in some examples, multiple ML techniques may be used.

In some examples, the computing device 107 may receive an identification of a video from user input through a GUI. For example, referring again to FIG. 5, the example GUI 500 provides functionality to enable a user to create, remove, or edit bookmarks in a video. To use the GUI 500 to identify a video frame, the user may use the video controls 416a-c to manually scrub through the surgical video 471 to identify the particular frame of interest, whether the beginning of a step, sub-step, or event of interest. The user may then select the "Add New Bookmark" option to provide an indication to the computing device 107 of the video frame within the surgical video 471.

While video frames may be identified using ML techniques or user input, other techniques may be employed as well. For example, after a type of surgical procedure for a video has been identified, the computing device 107 may divide the video into multiple segments of equal length based on the number of steps associated with the identified surgical procedure. For example, if the surgical video is two hours and the surgical procedure in the video has eight steps, the computing device 107 may then divide the surgical video into eight equal segments and identify a video frame corresponding to the beginning of each of the eight segments. For example, the computing device 107 may identify video frames at 0:00.0, 0:15.0, 0:30.0, 0:45.0, 1:00.0, 1:15.0, 1:30.0, and 1:45.0.

In another example, the computing device 107 may employ information indicating the average length of time per step of a particular surgical video to identify frames of video. For example, if a particular surgical procedure has five steps, and on average the steps take 12 minutes, 20 minutes, 45 minutes, 30 minutes, and 6 minutes, the computing device 107 may identify corresponding frames based on those durations, or, based on ratios of the average step lengths to the duration of the video. For example, the 12-minute step represents 10.6% of the length of the surgery. Thus, if the surgical video is two hours long, the computing device 107 may identify a frame at 12:43.5 (for 24 fps) as the beginning of the second step.

Other techniques may be employed as well. For example, bookmarks may be added based on events occurring within the surgical procedure, such as changing a tool, detected events or complications, performing a particular technique (e.g., performing a particular type of suture) or activating a particular tool (e.g., a cautery tool), etc. Such events may be identified by an ML technique or based on inputs received from the robotic surgical system. For example, when a tool is removed from the surgical robot or a new tool is used, the surgical robot may generate a signal that the system 100 may use to annotate the surgical video with metadata or create one or more bookmarks.

In some examples, one or more video frames may be determined in real-time. For example, during a surgical procedure, a surgeon may identify the beginning of a new step of the surgical procedure. In this example, the surgeon may say something to indicate that a new step is beginning. The surgeon's voice may be captured by the system's microphone 112, and the computing device 107 may use a voice recognition technique to recognize the surgeon's speech and recognize an indicator of a new step in the surgical procedure. For example, the surgeon may speak a voice command, e.g., "begin new step," or he may state the name of the new step, e.g., "creating a JJ anastomosis," etc. The computing device 107 may recognize such speech as indicating a new step of the surgical procedure and determine a corresponding video frame. For example, the computing device 107 may identify the video frame corresponding to the time the surgeon's speech input began, or to the time the surgeon's speech input ended. Further, such functionality may be invoked, even if the system 100 is unable to recognize the speech. For example, the system 100 may identify a video frame based solely on the presence of detected, but unrecognized speech. This may enable identification of a bookmark on the premise that a spoken command indicates the presence of noteworthy content.

In addition to (or instead of) voice inputs, the surgeon may perform a gesture indicating a new step of the surgical procedure has begun. For example, the surgeon may perform a movement with one or more of the user controls for the surgical robot associated with a particular step of the surgical procedure. Such user controls may include hand controls, foot pedals, etc. according to different examples. Such as by disengaging control of a surgical tool, and then performing a movement with the controller. Or the user may input a gesture using a touch-sensitive input device, e.g., by making a gesture on the computing device's touch screen 111. For example, the user may swipe horizontally with two fingers to indicate a new step is beginning. The time at which the gesture is detected may be used to identify a frame of video having a corresponding timestamp. In some examples, the system may employ gaze tracking to monitor a user's gaze direction or focus. The system may detect the user's gaze as being directed to a predefined location, such as user interface component, to bookmark a video frame. While the examples above provide certain techniques to identify one or more video frames, still further approaches to autonomously identifying video frames may be employed.

At step 1330, the computing device 107 generates a bookmark based on the identified video frame. In this example, the computing device 107 generates metadata that indicates a bookmark and includes an identifier for the identified video frame corresponding to the bookmark. For example, FIG. 6 illustrates example metadata 600 that includes identifiers for frames of video corresponding to the respective bookmark. Referring to FIG. 6, bookmark 622a includes identifiers for a bookmark, which include <bookmark> and </bookmark> tags. In addition, the bookmark 622a includes a <begin> tag that identifies a specific video frame, 3:12.0, within the surgical video. Thus, the computing device 107 has generated a bookmark based on the identified video frame.

In some examples, the computing device 107 may generate richer bookmarks than only identifying a video frame for the bookmark. For example, as discussed above, the computing device 107 may employ one or more ML techniques to recognize the type of the surgical procedure within the surgical video 471, and to identify steps, sub-steps, or events of interest within the surgical video 471. Such information may also be included within the bookmark, such as is shown in FIG. 6. As discussed above, the information relating to the type of the surgical procedure or the steps, sub-steps, and events may be standardized to provide uniform identifiers across an entire corpus of surgical videos.

In addition to, or instead of, employing automated techniques to recognize information about the surgical video to include within one or more bookmarks, the computing device 107 may request user input to be included with a bookmark. For example, the computing device 107 may prompt a user to provide a name for a bookmark; select a type of surgical procedure; select one or more steps, sub-steps, or events; enter other user-specific information, etc. Further, in some examples, if an ML technique fails to recognize a surgical procedure type, or a step, sub-step, or event, the computing device 107 may prompt the user to provide the missing information. For example, FIG. 5 illustrates an example GUI 500 in which the user is prompted to enter step information for bookmark 422e.

In some examples, bookmark information may be generated at multiple different times, with subsequent information being added to the generated bookmark. For example, during surgery, the surgeon may designate a frame of video as discussed above, which may cause the computing device 107 to create a bookmark for the video frame. At a later time, the surgical video may be provided to one or more ML techniques to recognize the type of the surgical procedure as well as steps, sub-steps, or events within the surgical video. As each ML technique analyzes the surgical video, it may update existing bookmark information, or it may output information that the computing device 107 can incorporate into existing bookmarks (or create new bookmarks, as appropriate if no corresponding bookmark exists).

At block 1340, the computing device 107 associates the bookmark with the video frame. In this example, the computing device 107 associates the bookmark with the video frame by identifying the video frame within the definition of the bookmark, as shown in FIG. 6. For example, bookmark 622a is associated with frame 3:02.0 by the <begin> tag. In addition, the bookmark is associated with the video frame based on the <video> tag, which identifies the video associated with the metadata 600 that defines bookmark 622a. Thus, in this example, an association between the bookmark and the video frame is created based on the identified video and the identified video frame.

While, the example shown in FIG. 6 employs metadata stored in a file separate from the video file(s) of the surgical video, in some examples as discussed above, the metadata may be stored within the video file itself. For example, the video file may include metadata in a beginning portion of the file before the video information. In one such example, the bookmark may simply reference the specific video frame, such as shown in FIG. 6. In another example, the metadata for a surgical video may be interleaved with the video frames themselves. Thus, when a video player encounters a frame with metadata, the metadata is extracted.

At block 1350, the computing device 107 stores the bookmark. In this example, the computing device 107 stores metadata including the bookmark on the data store 133 as in a file separate from the video file(s), though as discussed, in some examples, the metadata may be stored within the video file(s) itself. Further, other examples may employ cloud storage, e.g., the system 1100 of FIG. 11, to store metadata, including bookmarks.

After completing block 1350, the method 1300 may proceed to block 1360, or it may return to block 1320 to identify another video frame for bookmarking. It should be appreciated that any number of bookmarks may be created for a particular surgical video, and therefore the method 1300 may return to block 1320 any number of times.

At block 1360, the computing device 107 receives user input to share a portion of the surgical video. For example, referring to the GUI 1000 shown in FIGS. 10A-10B, the user may select one or more bookmarks 422a-e and either select the share video segment(s) button 1010 or call the context-sensitive menu 1020 and select a sharing option.

Referring again to FIG. 10B, the GUI 1000 provides options the user may select to provide user input to share a portion of the surgical video 471. For example, the user can select how to share the video, e.g., as segment(s) only or share the entire video with the selected bookmark (or pin). The user may also specify a recipient list or channel(s). To initiate the sharing operations, the user may then select the "Share" button.

In some examples, other techniques may be used to select a video segment to share. For example, an example GUI may allow a user to select a contact, group of contacts, channel, etc., e.g., from a drop-down list of contacts, and then drag one or more bookmarks onto the contact to share the bookmark(s) with the selected contact (or group of contacts, channel, etc.).

At block 1370, the computing device 107 transmits a message to the selected recipient(s) or channel to share the selected portion of the surgical video. In this example, the computing device 107 generates and transmits an email that includes an attachment having the selected portion of the surgical video that has been extracted from the full surgical video. In some examples, however, the computing device 107 may transmit a message having a reference to a stored copy of the portion of the surgical video. For example, the computing device 107 may extract the portions of the surgical video to be shared (as will be discussed in detail below with respect to FIG. 14) and generate a reference, e.g., a URL, identifying the location of the extracted portions of the surgical video. Further, in some examples, the computing device 107 may transmit a link to the entire surgical video and information indicating a starting location for the video cursor corresponding to the selection portion of the surgical video to be shared. Thus, when the recipient accesses the link, the surgical video is accessed and the recipient is presented with the surgical video with the video cursor 414 positioned at the shared portion of the surgical video. Still further techniques to transmit a message may be employed according to different examples.

Figure 14:
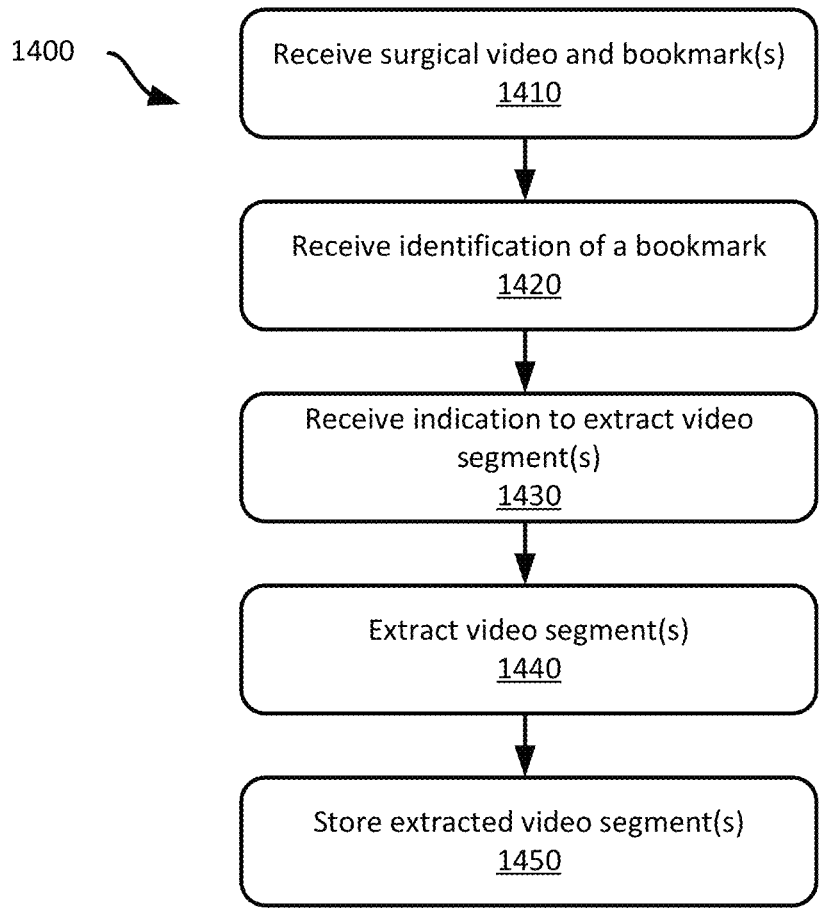

Referring now to FIG. 14, FIG. 14 shows an example method 1400 for segmenting surgical videos. This example method 1400 will be described with respect to the example system 100 shown in FIG. 1; however it should be appreciated that any suitable system may be employed, such as the systems shown in FIG. 2, 3A-3B, or 11.

At block 1410, the computing device 107 receives a surgical video and at least one bookmark. The computing device receives surgical video generally as discussed above with respect to block 1310 of FIG. 13. In this example, the computing device 107 receives the at least one bookmark as metadata stored in a separate file from the surgical video; however, in some examples, the computing device 107 may receive the at least one bookmark as metadata embedded within the surgical video. It should be appreciated that in some examples, the computing device 107 receives a surgical video without any bookmarks and then receives one or more bookmarks based on a user performing another method according to this disclosure, such as the example method 1300 of FIG. 13. Thus, block 1410 may be performed by performing blocks 1310-1350 of the method 1300 of FIG. 13 (or similar methods according to this disclosure).

At block 1420, the computing device 1420 receives an identification of a bookmark. In this example, a user accesses a GUI provided by a web portal application, such as the GUI 900 shown in FIG. 9A. In some examples, however, the GUI 900 may be provided by an application executing locally on the computing device 107. After accessing the GUI 900, the user selects one or more bookmarks defined for the surgical video, such as one or more of the bookmarks 422a-e defined surgical video 471. For example, the user may select one or more bookmark by touching a touch-sensitive display at locations corresponding to the bookmark indicator(s) displayed on the timeline 414 or in the list of bookmarks, or the user may use a mouse to select one or more of the bookmarks 422a-e.

In some examples, rather than receiving a user selection, the computing device 107 may employ bookmarks output by an ML technique that has identified one or more steps, sub-steps, or events within the video. For example, the computing device 107 may receive identifications of video frame within the surgical video generally as discussed above with respect to block 1320 of FIG. 13. The computing device 107 may then identify one or more of the identified video frames as the identification of a bookmark. For example, the computing device 107 may identify all video frames for steps of the surgical procedure, but not video frames for sub-steps or events within the surgical procedure. In some examples, however, the computing device 107 may identify all video frames identified by the ML technique as indicating steps, sub-steps, or events.

There is no limitation implied that a bookmark identified at block 1420 is a bookmark previously defined for the surgical video. For example, a user may scrub through a received video, e.g., a video with no bookmarks, and add one or more bookmarks, such as described above with respect to the method 1300 of FIG. 13, and then at block 1420 select one of the newly created bookmarks. Further in some examples, a user may select a segment of video, such as by selecting the video cursor 414, right-clicking on it (or press-and-hold on a touch screen) to begin selecting video frames, and drag the cursor 414 to a new location to select the desired range of video frames. The start and end locations of such a selection may be established as one or more bookmarks, at least temporarily, to enable extraction of the selected portion of the surgical video.

At block 1430, the computing device 107 receives an indication to extract a portion of the surgical video. After selecting a bookmark, the GUI may present an option to extract one or more video segments. For example, as shown in FIG. 9B, a user may select a bookmark 422b and the GUI 900 may present a context-sensitive menu 930 near (or proximate) the bookmark 422b with selectable options to extract individual video segments or a single video, or they may select one of the static button options 910, 920.

However, as discussed above, in some examples, the computing device 107 may identify one or more bookmarks based on video frames identified by one or more ML techniques. After receiving the identification of the video frames, the computing device 107 may initiate extraction of one or more video segments. Thus, the computing device 107 may receive an indication to extract a portion of the surgical video based on receiving one or more identified video frames from one or more ML techniques.

At block 1440, the computing device 107 extracts a portion of the surgical video beginning at a selected bookmark. In this example, the computing device 107 extracts individual video segments based on the selected bookmarks. To extract the video segments, the computing device 107 identifies each selected bookmark and then determines the next bookmark associated with the surgical video of a same hierarchical level in the bookmarks associated with the surgical video.

In the example shown in FIGS. 9A-9B, if the user selects bookmark 422b, the computing device 107 determines the next bookmark at the same hierarchical level (the "ending" bookmark), which in this example is bookmark 422c. However, referring to the example hierarchy 700 shown in FIG. 7, if the user selects step 1 (710), the computing device 107 may determine the next bookmark at the same hierarchical level as being step 2 (720). Thus, the computing device 107 selects video frames associated with the selected bookmark as well as any nested bookmarks. Similarly, if the user selects sub-step 2 (714), the computing device determines the next bookmark as being event 1 (716), thereby subsuming sub-steps A and B (714.1-.2) within the selection. Such an approach may allow a user to easily select a video segment at a particular level of granularity without requiring the user to individually select each nested bookmark within a particular segment of video.

After identifying the next bookmark at the same hierarchical level as the selected bookmark, the computing device 107 may create a new video file, access the file containing the surgical video 471, and copy video information from the surgical video 471 into the new video file beginning at the video frame corresponding to the elected bookmark and ending at the last frame before the ending bookmark, and including all intervening video frames. In this example, the computing device 107 also copies any metadata corresponding to the copied video frames. For example, if the metadata is stored in a separate file from the surgical video 471, the computing device 107 may create a second new file to store metadata, and copy metadata corresponding to the copied video into the second new file.

In some examples, a surgical video may have other corresponding information such as audio information, graphical overlays (e.g., comments, commentary, patient information such as pulse rate, blood pressure, etc.), etc., such information may also be copied into the new video file (or corresponding new file created along with the new video file) such that all information corresponding to the copied video is also copied into a new file or set of files.

In this example, the new video file is stored locally in non-volatile at the computing device 107, though in some examples, the new video file may be created in volatile memory for later storage in a non-volatile memory.

While the example extraction discussed above is with respect to a single selected bookmark, the example method 1400 also extracts video information associated with multiple selected bookmarks. If the user selects multiple bookmarks, the computing device 107 may perform block 1440 as discussed above for each selected bookmark. A user may invoke such functionality by selection an option like the "extract individual video segments" option 910 in FIGS. 9A-9B.

In some examples, the computing device 107 may determine if more than one of the selected bookmarks are consecutive bookmarks at the same hierarchical level (e.g., step 1 (710) and step 2 (720)), and if so, the computing device may extract a single video spanning all consecutive selected bookmarks at the same hierarchical level. For example, if the user selects bookmarks corresponding steps 1-3 (710-730) shown in FIG. 7, the computing device may extract a single video including video frames beginning at the video frame corresponding to the bookmark for step 1 (710) and ending at the last video frame before step 4 (740). Such functionality may be invoked if a user selects the "extract single video" option 920 in FIGS. 9A-9B.

In some examples, the computing device 107 may automatically extract one or more video segments based on video frames identified by one or more ML techniques. For example, an ML technique may identify video frames associated with different steps, sub-steps, or events within a surgical video. The computing device 107 may then select each video frame corresponding, for example, to each identified step and then, based on a configuration setting, either extract each step as a separate video segment, or extract each step, sub-step, and event as a separate video segment. In the latter example, the computing device may extract, for example, the video frames beginning at step 1 (710) in FIG. 7 to the video frame before step 2 (720), and also extract video segments for each of sub-step 1 (712), sub-step 2 (714), event 1 (716), sub-step A (714.1), and sub-step B (714.2). In such an example, the computing device 107 may thereby create seven separate video segments spanning each of these steps, sub-steps, and events. The different videos may then allow the viewer to select exactly the portion of the surgical video to be viewed. Similarly, such functionality may be invoked by a user in some examples by selecting each of the bookmarks corresponding to these steps, sub-steps, and events and selecting an option to extract individual video segments.

At block 1450, the computing device 107 stores the extracted video segment(s) to non-volatile storage. For example, the computing device 107 may store the extracted video segment(s) locally on a non-volatile storage medium, such as a hard drive, flash drive, etc. In some examples, the computing device 107 may store a copy of the extracted video on a remote storage device, such as in cloud storage or at a remote server, such as at data store 1142 or cloud storage 1150 shown in FIG. 11.

The method 1400 described above was described as having certain steps in certain orders; however, it should be appreciated that according to different examples, they steps may occur in different orders or may occur substantially simultaneously. For example, blocks 1440 and 1450 may occur substantially simultaneously. Further, the computing device may extract video at block 1440 while a user selects another bookmark at block 1420.

Figure 15:
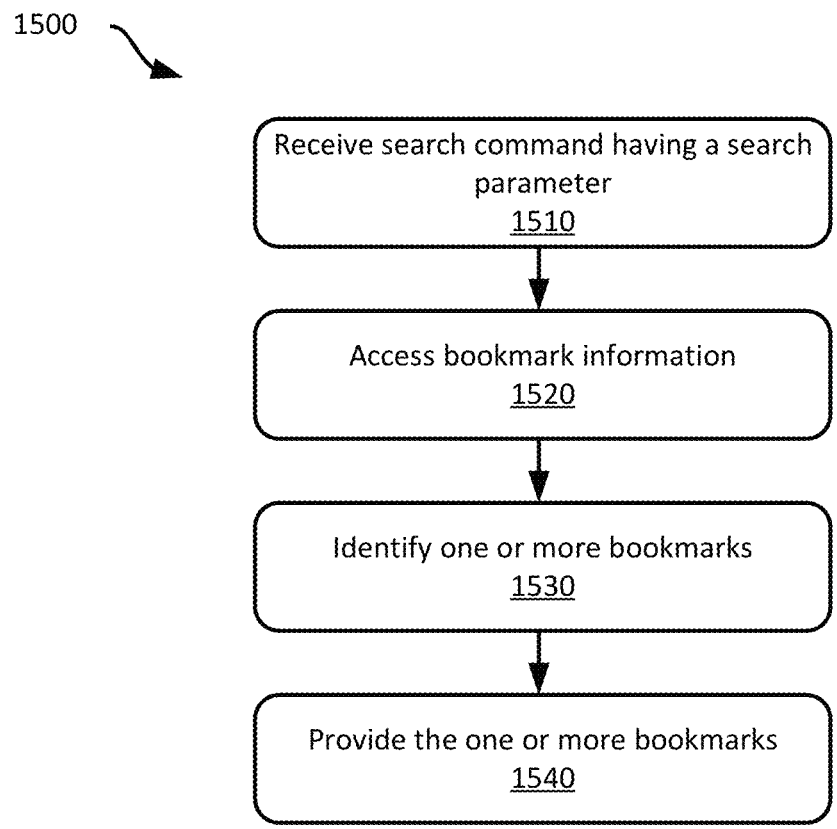
FIG. 15 shows an example method for searching for surgical video segments.

Referring now to FIG. 15, FIG. 15 shows an example method 1500 for searching for surgical video segments. This example method 1400 will be described with respect to the example system 1100 shown in FIG. 11; however it should be appreciated that any suitable system may be employed, such as the systems shown in FIG. 1, 2, or 3A-3B.

At block 1510, the server 1140 receives a search command having at least one search parameter. For example, the user may interact with the GUI 1200 shown in FIG. 12A to input one or more search parameters via a web portal provided by the server 1140. In this example, the user may select a procedure from the drop-down list of procedures 1210 or a step or sub-steps or event from the respective drop-down lists 1220, 1230. As discussed above, each of these lists may include lists of standardized procedure, step, and event names. For example, gastric bypass procedures may be represented by the standard procedure name "Gastric Bypass." Thus, a user may simply select the desired procedure without needing to enter keywords that may or may not match user-defined procedure or step names. As discussed above, bookmarks may be established using standardized names, which may then be used to populate the procedure, step, and event lists 1210-1230 shown in the example GUI 1200. In addition, or alternatively, the user may enter one or more keywords in the keyword text field area 1240.

After the user enters each of the search terms, she may press the "search videos" button 1250 to send a search command to the server 1140. The server 1140 receives the search command and any search parameters, such as those entered by the user. In some examples, the server 1140 may forward the search command to the data store 1142 or to the cloud storage 1150, which may include a database management system ("DBMS"); however, in some examples, the server 1140 itself may perform the search using the search parameters.

At block 1520, the server 1140 accesses bookmark information associated with one or more surgical videos stored in the data store 1142 or cloud storage 1150. For example, the server 1140 may provide the DBMS for the data store 1142 or cloud storage 1150. The DBMS may have records for one or more surgical videos and associated metadata. Further, DBMS may index the surgical videos based on one or more bookmarks stored within the metadata. Thus, the DBMS may access the bookmark information via such indices or other DBMS database constructs.

At block 1530, the server 1140, using the DBMS, identifies one or more bookmarks based on the received search parameters based on the identified surgical procedure, steps, or events. For example, the server 1140, using the DBMS, may identify all videos matching the identified surgical procedure (if any), and identify one or more bookmarks associated with such videos that match the steps, sub-steps, or events identified within the search parameters. In some examples search parameters may include other information, such as surgical tools, doctors, date ranges, etc. that may be stored in metadata annotations or bookmarks associated with the surgical video.

At block 1540, the server 1140 provides one or more bookmarks to the user via the web portal. Referring again to FIG. 12B, the GUI 1200 may provide a search results window 1260 in which search results are displayed. The example GUI 1200 in FIG. 12B shows three search results 1262-1266 represented by icons with brief bibliographic information. The search results 1262-1266 may include full surgical videos cued to begin at the "Create JJ Anastomosis" step as specified in the search parameters, or they may include video segments extracted from a full surgical video, such as by the processes described above with respect to FIG. 14 (or any suitable method according to this disclosure). Thus, the user may quickly and efficiently identify surgical videos, and in particular, specific portions of surgical videos matching their search criteria to enable the user to quickly find relevant videos or portions of videos based on previously defined bookmarks, such as bookmarks created according to various systems and methods described herein.

It should be appreciated that after performing an example method according to FIG. 15, the system may then allow the user to perform one or more methods according to this disclosure on the videos returned from the search, including the methods according to FIG. 13 or 14. For example, after obtaining search results, the user may select one or more bookmarks for video playback, to share with another user, or to extract one or more video segments. Further, it should be appreciated that the methods of FIGS. 13-15 may be combined in other ways as well. For example, a user may perform a method according to FIG. 14 to extract a video segment, and may then perform steps 1360 and 1370 according to FIG. 13 to share the extracted video segment. Thus, while the methods illustrate certain discrete functions enabled by various systems according to this disclosure, each of these methods are only aspects of the available functionality and may be combined to provide systems or methods to annotate, bookmark, extract, share, or search for surgical video.

Figure 16:
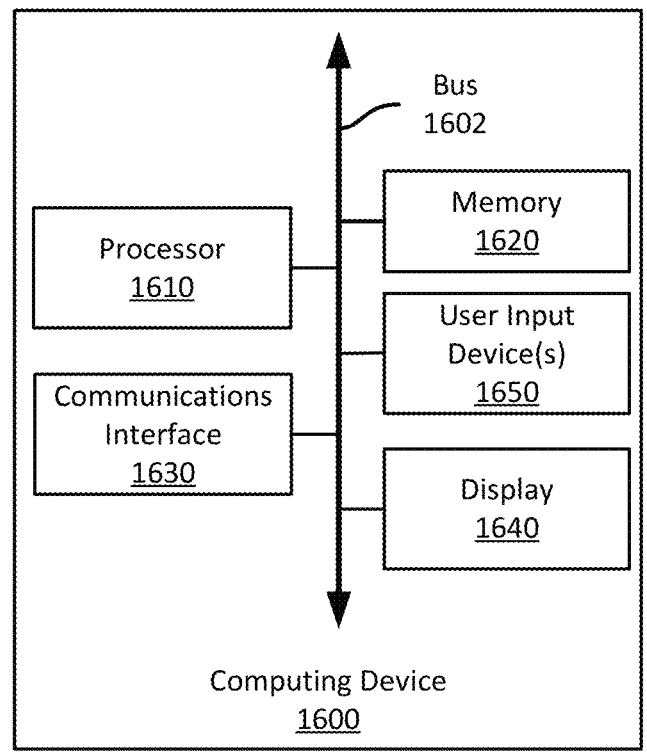
FIG. 16 shows an example computing device suitable for use with systems and methods according to this disclosure.

Referring now to FIG. 16, FIG. 16 shows an example computing device 1600 suitable for use in example systems or methods for segmenting surgical videos according to this disclosure. Suitable computing devices may include or take the form of desktop or laptop computers, tablets, smartphones, phablets, wearable devices, augmented or virtual reality devices, thin clients, etc. The example computing device 1600 includes a processor 1610 which is in communication with the memory 1620 and other components of the computing device 1600 using one or more communications buses 1602. The processor 1610 is configured to execute processor-executable instructions stored in the memory 1620 to perform one or more methods for segmenting surgical videos according to different examples, such as part or all of the example methods 1300-1500 described above with respect to FIGS. 13-15. The computing device, in this example, also includes one or more user input devices 1650, such as a keyboard, mouse, touchscreen, microphone, etc., to accept user input. The computing device 1600 also includes a display 1640 to provide visual output to a user.

The computing device 1600 also includes a communications interface 1640. In some examples, the communications interface 1630 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure.

The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   receiving, by a processor of a computing device, surgical video, the surgical video comprising at least a sequence of video frames captured by an endoscope during an endoscopic surgical procedure;
   recognizing one or more steps of the surgical video by the processor using a trained ML technique;
   identifying one or more video frames of the surgical video corresponding to the recognized steps;
   in response to identification of the one or more video frames, generating one or more bookmarks based on the one or more steps of the surgical video and the one or more video frames;
   associating, by the processor, the one or more bookmarks with the respective one or more video frames; and
   storing, by the processor, the one or more bookmarks.

2. The method of claim 1, further comprising:
   determining, by the processor, an event in the surgical video; and
   determining the identification of the video frame based on the event.

3. The method of claim 2, wherein the event comprises one of changing a surgical robotic tool or activating a surgical robotic tool.

4. The method of claim 1, further comprising:
   receiving, by the processor, audio information from a microphone; and
   determining the identification of the video frame based on the audio information.

5. The method of claim 4, further comprising recognizing, by the processor using a speech recognition technique, one or more spoken words from the audio information; and
   determining the identification of the video frame based on the one or more spoken words.

6. The method of claim 4, wherein the audio information is received during the endoscopic surgical procedure and wherein determining the identification of the video frame happens substantially in real-time during the endoscopic surgical procedure.

7. The method of claim 1, further comprising:
   receiving, by the processor, input information from an input device; and
   determining the identification of the video frame based on the input information.

8. The method of claim 7, further comprising:
   determining, by the processor, a gesture based on the input information; and
   wherein determining the identification of the video frame is based on the gesture.

9. The method of claim 1, further comprising:
   receiving, by the processor, input information from an input device;
   generating an additional bookmark based on the input information; and
   storing the additional bookmark.

10. A method comprising:
    receiving, by a processor of a computing device, a surgical video having a bookmark;
    receiving a selection of the bookmark;
    receiving an indication to share a segment of the surgical video and a recipient, the segment of the surgical video based on the bookmark;
    extracting a portion of the surgical video based on the bookmark;
    storing the extracted portion of the surgical video; and
    providing the stored extracted portion of the surgical video to the recipient.

11. The method of claim 10, wherein the surgical video has a plurality of bookmarks and the bookmark is a first bookmark of the plurality of bookmarks, and further comprising:
    receiving a selection of a second bookmark of the plurality of bookmarks; and
    wherein extracting the portion of the surgical video is further based on the second bookmark.

12. The method of claim 11, further comprising:
    receiving, by the processor, input information from an input device; and
    generating the second bookmark based on the input information.

13. The method of claim 10, wherein the bookmark corresponds to a frame in the surgical video, and further comprising receiving a scrubbing input to change the bookmark to a different frame in the surgical video.

14. The method of claim 10, wherein the recipient comprises a user, and wherein providing the extracted portion of the surgical video comprises one or more of emailing a link to the portion of the surgical video to the recipient or emailing a copy of the extracted portion of the surgical video to the recipient.

15. The method of claim 10, wherein the recipient comprises a web portal and providing the extracted portion of the surgical video to the recipient comprises posting the extracted portion of the surgical video to the web portal.

16. A system comprising:
    a non-transitory computer-readable medium; and
    one or more processor communicatively coupled to the non-transitory computer-readable medium, the processor configured to execute processor-executable instructions stored in the non-transitory computer-readable medium to:
    receive surgical video, the surgical video comprising at least a sequence of video frames captured by an endoscope during an endoscopic surgical procedure;
    recognize one or more steps of the surgical video by the processor using a trained ML technique;
    identify one or more video frames of the surgical video corresponding to the recognized steps;
    in response to identification of the one or more video frames, generate one or more bookmarks based on the one or more steps of the surgical video and the one or more video frames;
    associate the one or more bookmarks with the respective one or more video frames; and
    store the one or more bookmarks.

17. The system of claim 16, wherein the processor is configured to execute further processor-executable instructions stored in the non-transitory computer-readable medium to:
determine an event in the surgical video; and
determine the identification of the video frame based on the event.

18. The system of claim 17, wherein the event comprises one of changing a surgical robotic tool or activating a surgical robotic tool.

19. The system of claim 16, wherein the processor is configured to execute further processor-executable instructions stored in the non-transitory computer-readable medium to:
receive audio information from a microphone; and
determine the identification of the video frame based on the audio information.

20. The system of claim 19, wherein the processor is configured to execute further processor-executable instructions stored in the non-transitory computer-readable medium to:
recognize, using a speech recognition technique, one or more spoken words from the audio information; and
determine the identification of the video frame based on the one or more spoken words.

21. The system of claim 20, wherein the audio information is received during the endoscopic surgical procedure and wherein determination of the identification of the video frame happens substantially in real-time during the endoscopic surgical procedure.

22. The system of claim 16, wherein the processor is configured to execute further processor-executable instructions stored in the non-transitory computer-readable medium to:
receive input information from an input device; and
determine the identification of the video frame based on the input information.

23. The system of claim 22, wherein the processor is configured to execute further processor-executable instructions stored in the non-transitory computer-readable medium to:
determine a gesture based on the input information; and
determine the identification of the video frame based on the gesture.

24. The system of claim 16, wherein the processor is configured to execute further processor-executable instructions stored in the non-transitory computer-readable medium to:
receive input information from an input device;
generate an additional bookmark based on the input information; and
store the additional bookmark.

25. A system comprising:
a non-transitory computer-readable medium; and
one or more processor communicatively coupled to the non-transitory computer-readable medium, the processor configured to execute processor-executable instructions stored in the non-transitory computer-readable medium to:
receive a surgical video having a bookmark;
receive a selection of the bookmark;
receive an indication to share a segment of the surgical video and a recipient, the segment of the surgical video based on the bookmark;
extract a portion of the surgical video based on the bookmark;
store the extracted portion of the surgical video; and
provide the stored extracted portion of the surgical video to the recipient.

26. The system of claim 25, wherein the surgical video has a plurality of bookmarks and the bookmark is a first bookmark of the plurality of bookmarks, and wherein the processor is configured to execute further processor-executable instructions stored in the non-transitory computer-readable medium to:
receive a selection of a second bookmark of the plurality of bookmarks; and
extract the portion of the surgical video further based on the second bookmark.

27. The system of claim 26, wherein the surgical video has a plurality of bookmarks and the bookmark is a first bookmark of the plurality of bookmarks, and wherein the processor is configured to execute further processor-executable instructions stored in the non-transitory computer-readable medium to:
receive input information from an input device; and
generate the second bookmark based on the input information.

28. The system of claim 25, wherein the processor is configured to execute further processor-executable instructions stored in the non-transitory computer-readable medium to receive a scrubbing input to scrub the bookmark to a frame in the surgical video.

29. The system of claim 25, wherein the recipient comprises a user, and wherein the processor is configured to execute further processor-executable instructions stored in the non-transitory computer-readable medium to:
email a link to the extracted portion of the surgical video to the recipient; or
email a copy of the extracted portion of the surgical video to the recipient.

30. The system of claim 25, wherein the recipient comprises a web portal and wherein the processor is configured to execute further processor-executable instructions stored in the non-transitory computer-readable medium to post the extracted portion of the surgical video to the web portal.

* * * * *